(12) United States Patent
Doshi et al.

(10) Patent No.: US 11,282,602 B2
(45) Date of Patent: Mar. 22, 2022

(54) DEVICE AND METHOD FOR MOBILE MONITORING OF DRAINAGE CATHETER

(71) Applicant: CareFusion 2200, Inc., San Diego, CA (US)

(72) Inventors: Palak Doshi, Evanston, IL (US); Shayna Massi, Palatine, IL (US); John A. Krueger, Muskego, WI (US)

(73) Assignee: CareFusion 2200, Inc., San Diego, CA (US)

( * ) Notice: Subject to any disclaimer, the term of this patent is extended or adjusted under 35 U.S.C. 154(b) by 968 days.

(21) Appl. No.: 15/334,561

(22) Filed: Oct. 26, 2016

(65) Prior Publication Data

US 2018/0113984 A1    Apr. 26, 2018

(51) Int. Cl.
  G16H 40/63  (2018.01)
  G16H 20/40  (2018.01)
  G16H 50/20  (2018.01)

(52) U.S. Cl.
  CPC .......... G16H 40/63 (2018.01); G16H 20/40 (2018.01); G16H 50/20 (2018.01)

(58) Field of Classification Search
  CPC ........ G16H 40/63; G16H 20/40; G16H 50/20
  USPC .......................................................... 705/2
  See application file for complete search history.

(56) References Cited

U.S. PATENT DOCUMENTS

| | | |
|---|---|---|
| 4,900,303 A | 2/1990 | Lemelson |
| 5,484,401 A | 1/1996 | Rodriguez et al. |
| 7,433,827 B2 * | 10/2008 | Rosenfeld ............... G16H 50/20 705/2 |
| 8,684,900 B2 * | 4/2014 | Tran ........................ A61B 8/488 600/3 |
| 2005/0203469 A1 | 9/2005 | Bobroff et al. |

(Continued)

FOREIGN PATENT DOCUMENTS

| | | |
|---|---|---|
| JP | 2009178551 A | 8/2009 |
| JP | 2010287237 A | 12/2010 |

(Continued)

OTHER PUBLICATIONS

International Search Report in counterpart International Application No. PCT/US17/57559, dated Jan. 2, 2018.

(Continued)

*Primary Examiner* — Robert A Sorey
*Assistant Examiner* — Kimberly A. Sass
(74) *Attorney, Agent, or Firm* — Dinsmore & Shohl LLP

(57) ABSTRACT

Devices and methods for mobile monitoring of a drainage catheter are provided. A device may be configured to perform an operation of rendering a user interface. The user interface may be configured to provide an output interface configured to prompt a user to input catheter use information, catheter use information being information related to using the catheter to drain fluid from the patient. The user interface may be configured to provide an input interface for the user to input catheter use information. The device may be further configured to receive catheter use information input by the user through the user interface. The device may be further configured to generate catheter management information based upon the received catheter use information. A method for mobile monitoring of a drainage catheter may include using a processor to perform the steps the device is configured to perform.

18 Claims, 25 Drawing Sheets

(56) References Cited

U.S. PATENT DOCUMENTS

| | | | |
|---|---|---|---|
| 2008/0004818 A1* | 1/2008 | Zaleski | G06F 19/00 |
| | | | 702/50 |
| 2009/0299363 A1 | 12/2009 | Saadat et al. | |
| 2012/0209165 A1 | 8/2012 | Degen et al. | |
| 2012/0259265 A1 | 10/2012 | Salehi et al. | |
| 2014/0090173 A1 | 4/2014 | DiMaio et al. | |
| 2014/0257047 A1 | 9/2014 | Sillay et al. | |
| 2015/0126976 A1 | 5/2015 | Tang et al. | |
| 2015/0342177 A1 | 12/2015 | Hassanein et al. | |
| 2016/0242666 A1 | 8/2016 | Pujar | |

FOREIGN PATENT DOCUMENTS

| | | | |
|---|---|---|---|
| JP | 2015515041 A | 5/2015 | |
| WO | 2013123086 A1 | 8/2013 | |
| WO | WO-2016049654 A1 * | 3/2016 | A61B 5/01 |

OTHER PUBLICATIONS

Written Opinion in counterpart International Application No. PCT/US17/57559, dated Jan. 2, 2018.

International Preliminary Report on Patentability dated Apr. 30, 2019 pertaining to International PCT Application No. PCT/US2017/057559.

Extended European Search Report dated May 12, 2020 relating to European Application No. 17865490.1.

Office Action dated Sep. 30, 2021 pertaining to Japanese Patent Application No. 2019-522504 (10 pages with English Translation).

* cited by examiner

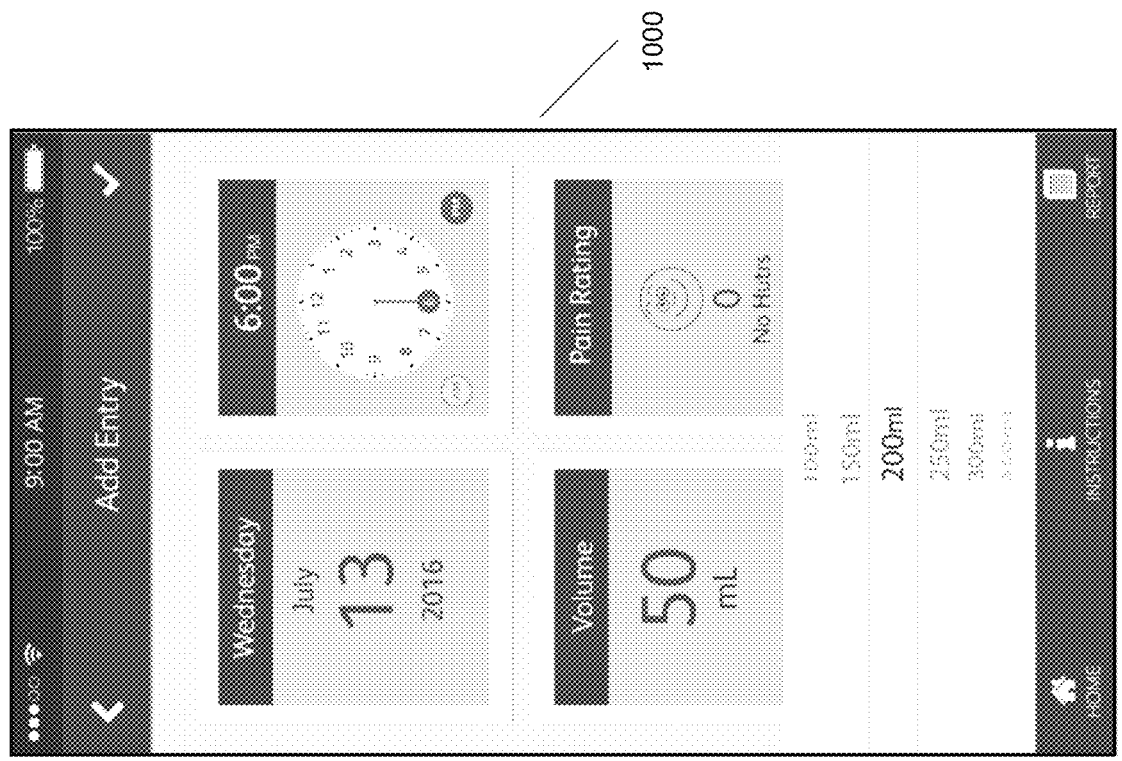
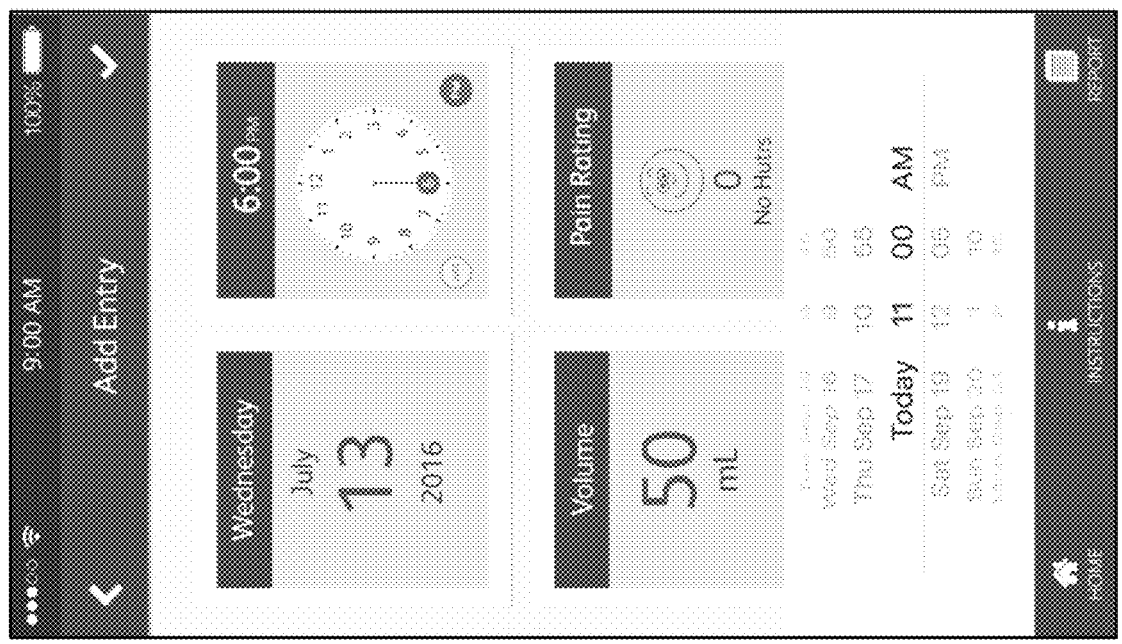
FIG. 10D
FIG. 10C

DEVICE AND METHOD FOR MOBILE MONITORING OF DRAINAGE CATHETER

TECHNICAL FIELD

Embodiments disclosed herein generally relate to medical devices. More particularly embodiments disclosed herein relate to devices and methods useful for monitoring and/or managing the use of a catheter to drain fluids from a body.

BACKGROUND

Fluid accumulation conditions can cause a patient a variety of unpleasant symptoms including pain, discomfort, bloating, shortness of breath, and coughing. For example, ascites describes an accumulation of fluid and other materials in the peritoneal or other body cavity. Pleural effusion refers to the effusion of fluid into the pleural space.

Fluid accumulation conditions such as ascites and pleural effusion may be treated by draining the excess fluid from an affected body cavity. Some methods of draining excess fluid from a body cavity involve implanting a catheter so that the catheter's distal end extends into the body cavity, and aspirating the excess fluid through the distal end, by applying a negative pressure at the catheter's opposite proximal end.

A suitable drainage apparatus 100 is shown partially disassembled in FIG. 1A. Apparatus 100 is shown in FIGS. 1B-1C as assembled and installed in a patient body (respectively, for pleural and peritoneal drainage) and includes a drainage container 114, typically a vacuum bottle. The drainage container 114 is removably attached by a proximal tube 110 at a valve 116 to a body-contacting distal catheter 112. The valve 116 may be configured in any number of ways known in the art for attaching catheters together in a fluid-patent manner, (which may include a two-part valve), and the proximal portion attached to the distal catheter 112 may be configured to be self-sealing when disconnected from the proximal tube 110. The distal end portion of the distal catheter 112 is shown indwelling the patient, disposed through the body wall 121 into an intra-body space 123b/123c, which may be—for example—a pleural cavity/space (e.g., FIG. 1B), peritoneal cavity/space (e.g., FIG. 1C), or other body cavity. That distal portion includes a sealing cuff 119 and a flexible fluid-intake length 115 including fenestrations 118 which—when the device is used—are located in the intra-body spaces 123b/123c. This structure may be better understood with reference to U.S. Pat. No. 5,484,401, which is incorporated herein by reference, and with reference to commercial products marketed under the name PleurX® by CareFusion® of San Diego, Calif. (a Becton Dickinson Company).

Often, although the step of implanting the catheter is performed by a physician, the drainage procedure is performed at home by the patient or by a caretaker. Symptom relief and patient outcome is dependent on regular drainage and proper post-procedure monitoring of factors such as drainage volume, drainage frequency, and the condition of the catheter site. Conventionally, clinicians require patients to record drainage volume and frequency on a paper log and bring the paper log with them to the follow-up appointment, where the clinician may also examine the catheter site. This conventional monitoring technology presents various technical problems.

For example, the patient may need to be physically transported, along with the paper log, to the clinician's office before the clinician can view the log or know the patient's treatment status. Accordingly, until the patient comes to the office, the clinician may not know, for example, whether the patient is maintaining a drainage log, whether the patient is complying with a prescribed drainage routine, whether the catheter site is in good condition, or whether the patient is exhibiting signs of developing a potentially harmful condition related to the drainage.

It may be desirable to provide improved devices and methods for monitoring and/or managing the use of a catheter to drain fluids from a body, which would provide patients and/or clinicians with improved convenience, more timely communication of relevant information, and/or a higher likelihood of compliance with prescribed drainage routines.

BRIEF SUMMARY

Devices and methods for mobile monitoring of a drainage catheter are provided. In one aspect, embodiments disclosed herein may include a non-transitory computer-readable medium storing instructions configured to be executed by a processor. The instructions may be configured to, when executed by the processor, cause the processor to perform an operation of rendering a user interface. The user interface may be configured to provide an output interface configured to prompt a user to input catheter use information, catheter use information being information related to using the catheter to drain fluid from the patient. The user interface may be further configured to provide an input interface for the user to input catheter use information. The instructions may be further configured to, when executed by the processor, cause the processor to perform an operation of receiving catheter use information input by the user through the user interface. The instructions may be further configured to, when executed by the processor, cause the processor to perform an operation of generating catheter management information based upon the received catheter use information.

In one aspect, embodiments disclosed herein may include a method for mobile monitoring of a catheter to drain fluid from a patient. The method may include rendering, by a processor, a user interface configured to provide an output interface configured to prompt a user to input catheter use information, catheter use information being information related to using the catheter to drain fluid from the patient. The user interface may be further configured to provide an input interface for the user to input catheter use information. The method may further include receiving, by a processor, catheter use information input by the user through the user interface. The method may further include generating, by a processor, catheter management information based upon the received catheter use information.

BRIEF DESCRIPTION OF THE DRAWINGS

FIGS. 10A, 10B, 10C, 10D, and 10E show an exemplary add entry page of a patient-side user interface;

DETAILED DESCRIPTION

Figure 1A:
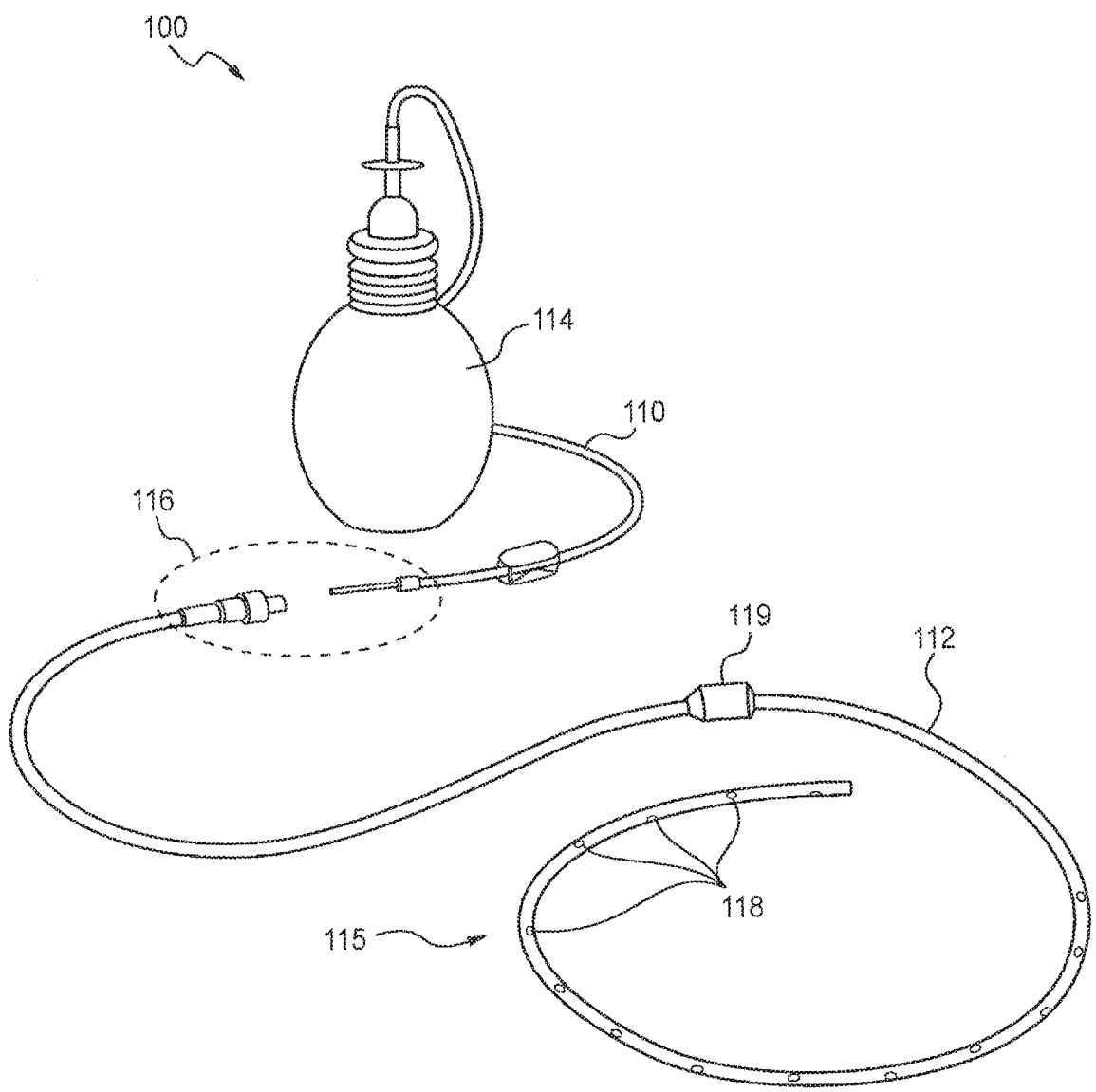
FIG. 1A shows an exemplary body cavity drainage catheter system including a vacuum bottle.
Figure 1C:
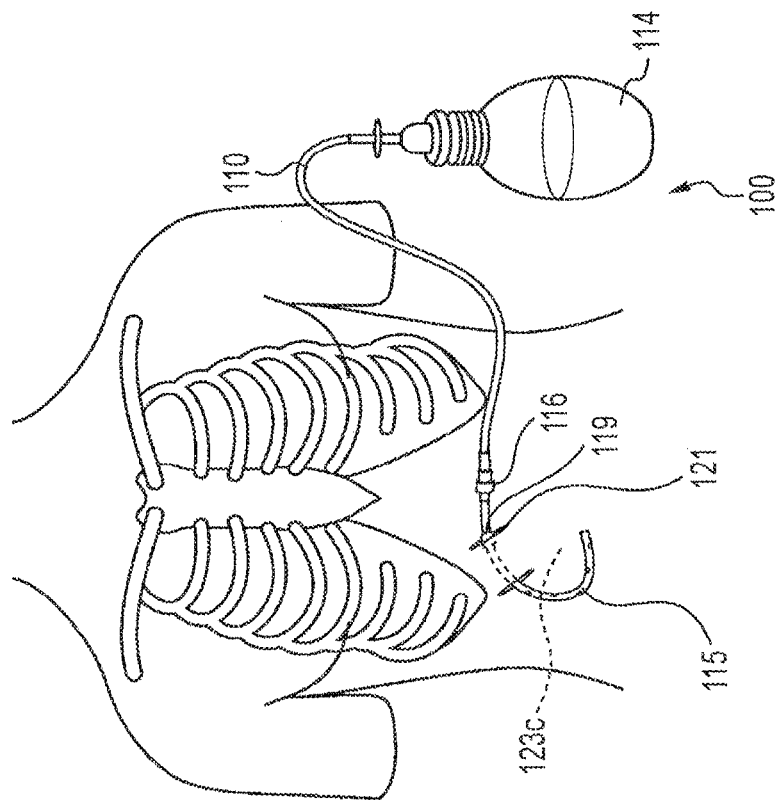
FIGS. 1B and 1C show, respectively, the system of FIG. 1A implemented for pleural drainage and peritoneal drainage.
Figure 1B:
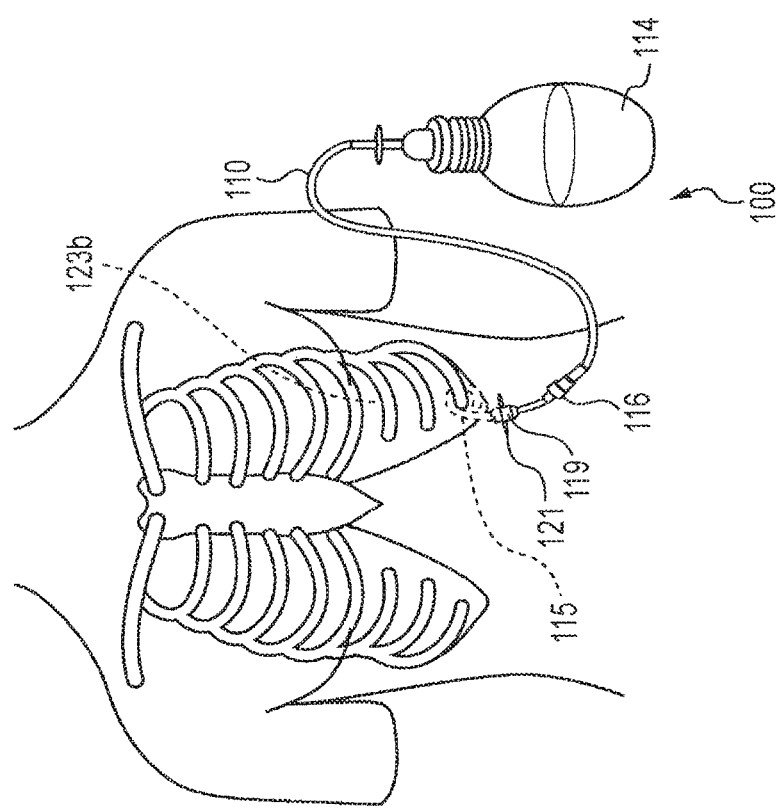

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. However, drawings may be rendered to scale unless specifically disclaimed.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE, or HIPAA standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

One embodiment of a system for monitoring and managing use of a catheter to drain fluid from a body is described with reference to FIG. 2. System 200 includes patient devices 201a-201n (where n may represent any number greater than one), server 202, physician device 203, and nurse device 204. Patient devices 201a-201n are generally configured to allow a user on the patient side of treatment (e.g. the patient or a caretaker of the patient) to input and receive information related to catheter-based fluid drainage. Physician device 203 is generally configured to allow a physician to input and receive information related to catheter-based fluid drainage. Nurse device 204 is generally configured to allow a nurse to input and receive information related to catheter-based fluid drainage. Server 202 is generally configured to receive information related to catheter-based fluid drainage from, and to transmit information to, patient devices 201a-201n, physician device 203, and nurse device 204.

In system 200, patient devices 201a-201n, physician device 203, and nurse device 204 are each in operative communication with server 202. The operative communication may be in the form of a network providing wired and/or wireless communication via recognized communication protocols, which allows patient devices 201a-201n, physician device 203, and nurse device 204 to transmit information to, and receive information from, server 202. Additionally, the network may similarly allow server 202 to transmit information to, and receive information from, patient devices 201a-201n, physician device 203, and nurse device 204.

Figure 2:
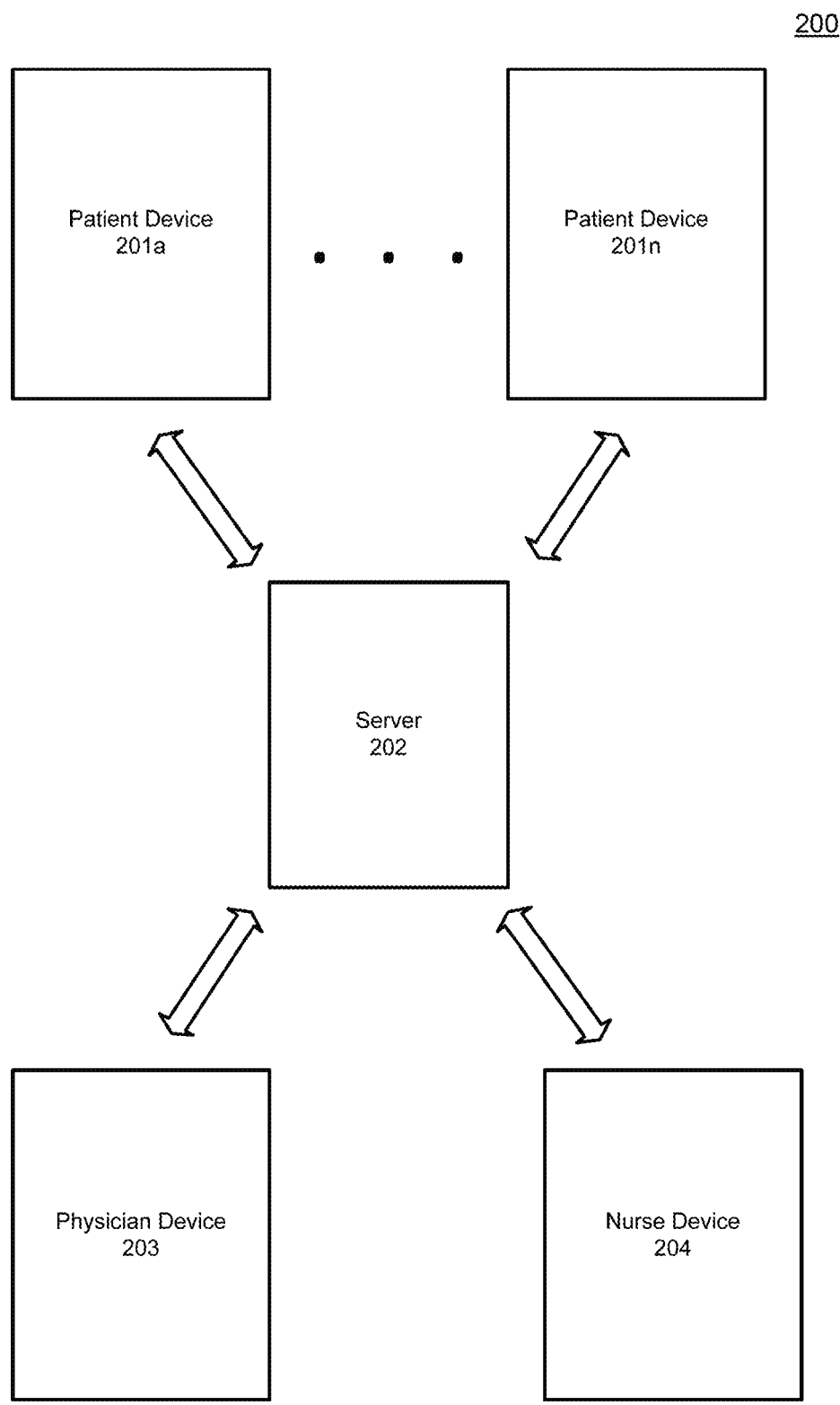
FIG. 2 shows an exemplary system for monitoring and managing the use of a catheter to drain fluid from a body.

Although system 200 as shown in FIG. 2 depicts a single server 202, a single physician device 203, and a single nurse device 204, other embodiments of a system for monitoring and managing the use of a catheter to drain fluid from a body may include more than one server 202, more than one physician device 203, and/or more than one nurse device 204. Additionally, other embodiments may include a single patient device 201*a*, and/or may omit the server 202, the physician device 203, and/or the nurse device 204.

Figure 3:
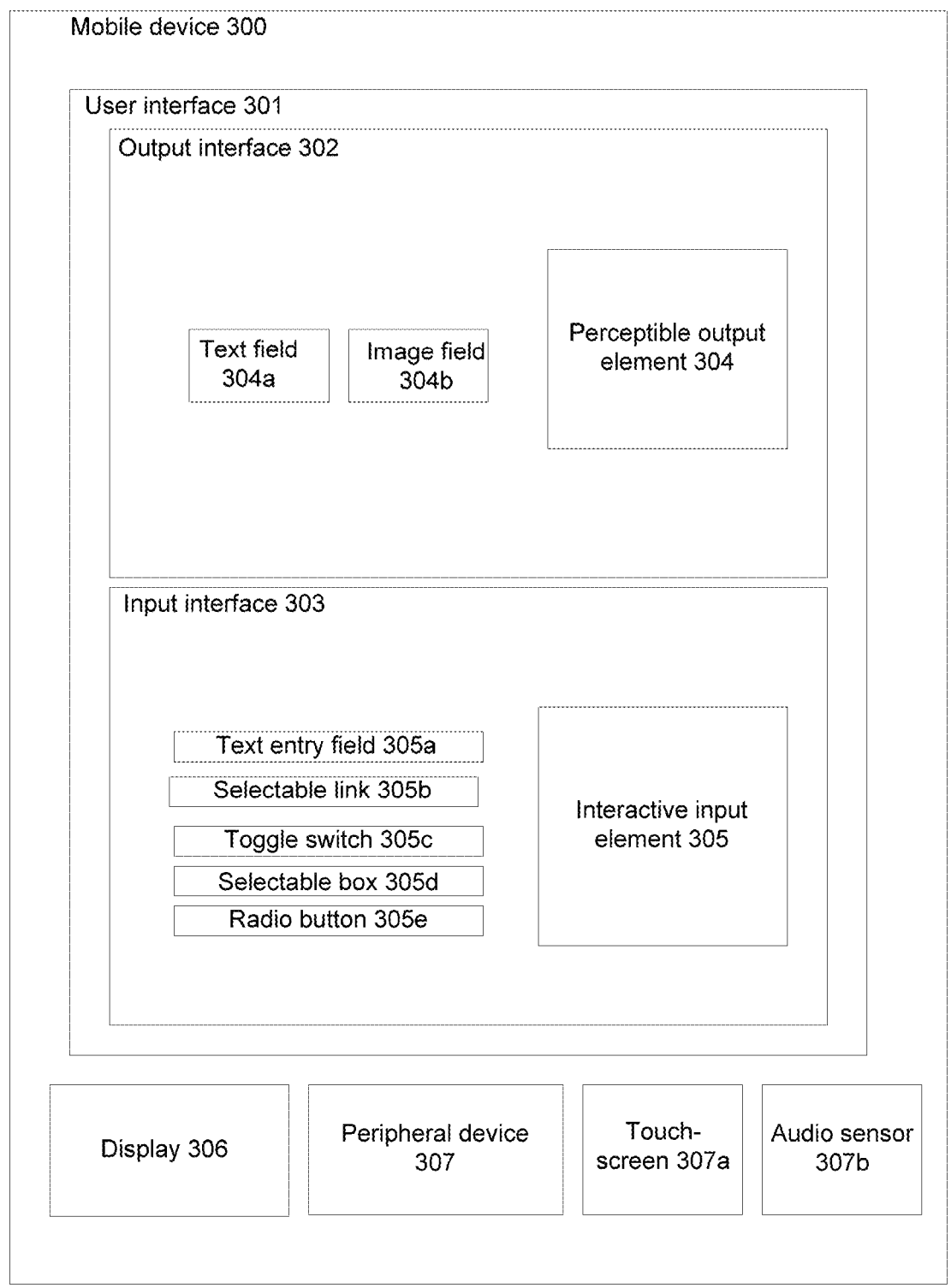
FIG. 3 shows an exemplary mobile device.

One embodiment of a device to implement patient device 201*a*, physician device 203, or nurse device 204 is described with reference to FIG. 3. Mobile device 300 is configured to generate and/or otherwise provide a user interface 301. For example, mobile device 300 may be configured to render user interface 301 for output on an output device of mobile device 300, based upon preexisting information and/or new information. For example, mobile device 300 may be configured to render user interface 301 for display on a display of mobile device 300 by using a preexisting user interface template, generating and using a new user interface, receiving and using a newly generated user interface, combining aspects of a preexisting user interface template with a newly received or generated user interface, or through combinations of such operations.

User interface 301 is configured to provide an output interface 302, by which mobile device 300 prompts a user to input catheter use information. Output interface 302 includes one or more perceptible output elements 304 configured to be output by mobile device 300 to request, remind, alert, inform, or otherwise prompt the user to input catheter use information into mobile device 300. User interface 301 is further configured to provide an input interface 303, through which the user is able to input catheter use information. Input interface 303 includes one or more interactive input elements 305 configured to be operated by the user to input catheter use information into mobile device 300.

Perceptible output element 304 may be embodied as an element of a graphical user interface displayable on display 306, and may include a text field 304*a* and/or an image field 304*b* having content associated with a particular type of catheter use information. Perceptible output element 304 may be embodied as an audio output signal having content associated with a particular type of catheter use information. Perceptible output element 304 may be associated with interactive input elements 305 so as to prompt the user to input a particular type of catheter use information using a particular interactive input element 305. Perceptible output element 304 may be located in, on, and/or adjacent to an associated interactive input element 305. Interactive input element 305 may be embodied as an element of a graphical user interface displayable on display 306, such as text entry field 305*a*, selectable link 305*b*, toggle switch 305*c*, selectable box 305*d*, and/or radio button 305*e*. Interactive input element 305 may be embodied as an element configured to recognize an audio input indicative of catheter use information. User interface 301 is configured to translate interactions with one or more peripheral devices 307 into interactions with input interface 303 and interactive input element 304. Peripheral device 307 may for example be embodied as one or more of a touch-screen 307*a* and/or an audio sensor 307*b* (e.g a microphone).

Referring again to FIGS. 2 and 3, an embodiment of patient device 201*a* may be implemented using mobile device 300. An embodiment of patient device 201*a* implemented using mobile device 300 is configured to prompt, using output interface 302, a patient-side user to input catheter use information, and to allow the patient-side user to input catheter use information using input interface 303. Catheter use information is information that is related to using the catheter to drain fluid from the patient.

Exemplary catheter use information may include: information about the patient who will have, is having, or has had fluid drained using a catheter; information about the catheter or related components that will be, are being, or have been used to drain fluid from the patient; information about the manner in which the catheter will be, is being, or has been used to drain fluid from the patient; and/or information about results of using the catheter to drain fluid from the patient.

Exemplary information about the patient may include information about the patient's name, gender, and/or age.

Exemplary information about the catheter or related components may include information about a type of or patient requirements for a catheter (e.g. chest vs. abdomen), drainage kit, and/or clamp (e.g. a pinch clamp vs. a roller clamp). Exemplary information about requirements for a catheter or related components may include an indication of the user's desire to purchase, or obtain a new prescription for, a catheter or related component.

Exemplary information about the manner of using the catheter may include: a drainage type (e.g. from the chest vs. from the abdomen), a prescribed drainage schedule, a date and/or time of drainage conducted, and/or a request for information about how to implement a step of using the catheter to drain fluid from the patient (e.g. a request input to device 201*a* from the user requesting that device 201*a* display instructions and/or instructional videos related to connecting the drainage bottle, draining fluid, and/or final steps and disposal, and/or a request input to device 201*a* from the user requesting that device 201*a* display a Frequently Asked Questions page and/or message board related to use of the catheter).

Exemplary information about results of using the catheter to drain fluid from the patient may include: volume drained from the patient; frequency of drainage from the patient; comfort or discomfort level of the patient (e.g. indications that the catheter site may be infected, indications of patient pain experience and/or pain rating, indications of shortness of breath, coughing, chest discomfort, and/or excessive saliva); information about the patient's ambulation ability (e.g. full, reduced, mainly site or lie down, mainly in bed, and/or totally bed bound); user notes about the drainage; and/or an image of a used drainage bottle and the fluid therein.

Referring again to FIGS. 2 and 3, an embodiment of patient device 201*a* implemented using mobile device 300 is further configured to receive the catheter use information that is input by the patient-side user through input interface 303 of user interface 301, and to generate catheter management information based upon the received catheter use information. Catheter management information includes information that the patient, caretaker, physician, nurse, or others could use to implement, alter, avoid, or treat the patient in connection with, use of the catheter to drain fluid from the patient.

Exemplary catheter management information may include: stored results of using the catheter to drain fluid from the patient; a recommendation of a step to be taken by the user to use the catheter to drain fluid from the patient; an indication of whether medical personnel should be contacted regarding the patient; and/or background information about using the catheter to drain fluid from the patient.

Exemplary stored results of using the catheter to drain fluid from the patient may include a historical log of drainage results over time.

Exemplary recommendations of a step to be taken by the user to use the catheter to drain fluid from the patient may include: a page configured to request a new prescription for a component of using the catheter to drain fluid from the patient; a page configured to order a component of using the catheter to drain fluid from the patient; instructions for how to use the catheter to drain fluid from the patient; and/or a page configured to access a video file related to using the catheter to drain fluid from the patient.

Exemplary indications of whether medical personnel should be contacted regarding the patient may include: a page indicating that a medical professional should be contacted regarding the patient; a page indicating that a medical professional need not be contacted regarding the patient; and/or a message that automatically contacts a medical professional regarding the patient.

Exemplary background information about using the catheter to drain fluid from the patient may include a discussion board and/or frequently asked questions (FAQ) page related to using the catheter for fluid drainage.

In an embodiment of patient device 201a implemented using mobile device 300, an embodiment of user interface 301 may be a graphical user interface including one or more patient pages configured to be displayed by display 306. Patient device 201a may be configured to generate and/or otherwise provide patient pages for display by display 306. For example, patient device 201a may be configured to render patient pages for display by display 306. Patient pages may each incorporate one or more perceptible output elements 304 and/or one or more interactive input elements 305. As will be described further below, some patient pages may be operatively connected with other patient pages, such that when the patient-side user interacts with an interactive input element 305 on one patient page, another patient page is provided and/or displayed by display 306. Exemplary patient pages with one or more of these features are shown in and described with reference to FIGS. 4-25.

Figure 4:
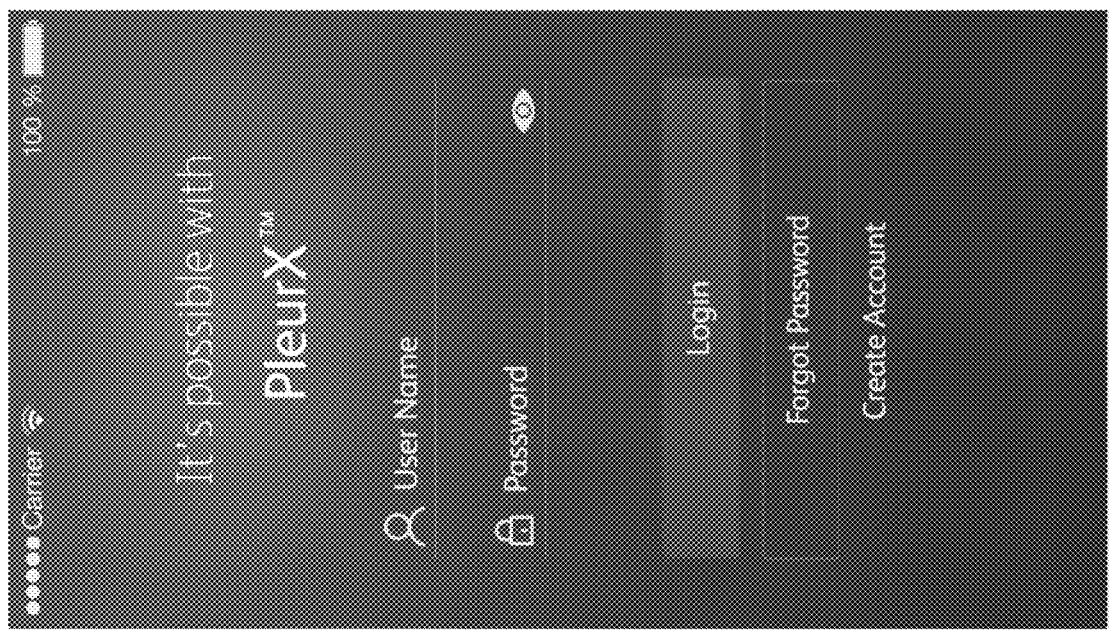
FIG. 4 shows an exemplary patient-side login page of a patient-side user interface.

One embodiment of a patient page is described with reference to FIG. 4. FIG. 4 depicts page 400, which is a patient-side log-in screen that is configured to prompt the user to enter a username and associated password. Page 400 may be configured to operate as a component of a unique patient portal. A unique patient portal may include access to different options, such as different prompts for catheter use information and different catheter management information, than is available in unique physician and nurse portals that are described further below. The unique patient portal may be a secure portal. For example, patient device 201a may be configured such that in order for a user to view any of the exemplary patient pages of FIGS. 4-25 that display or allow the user to input catheter use information associated with a patient, the user must first enter a username associated with that patient along with a password that patient device 201a recognizes as being associated with that patient.

Figure 5:
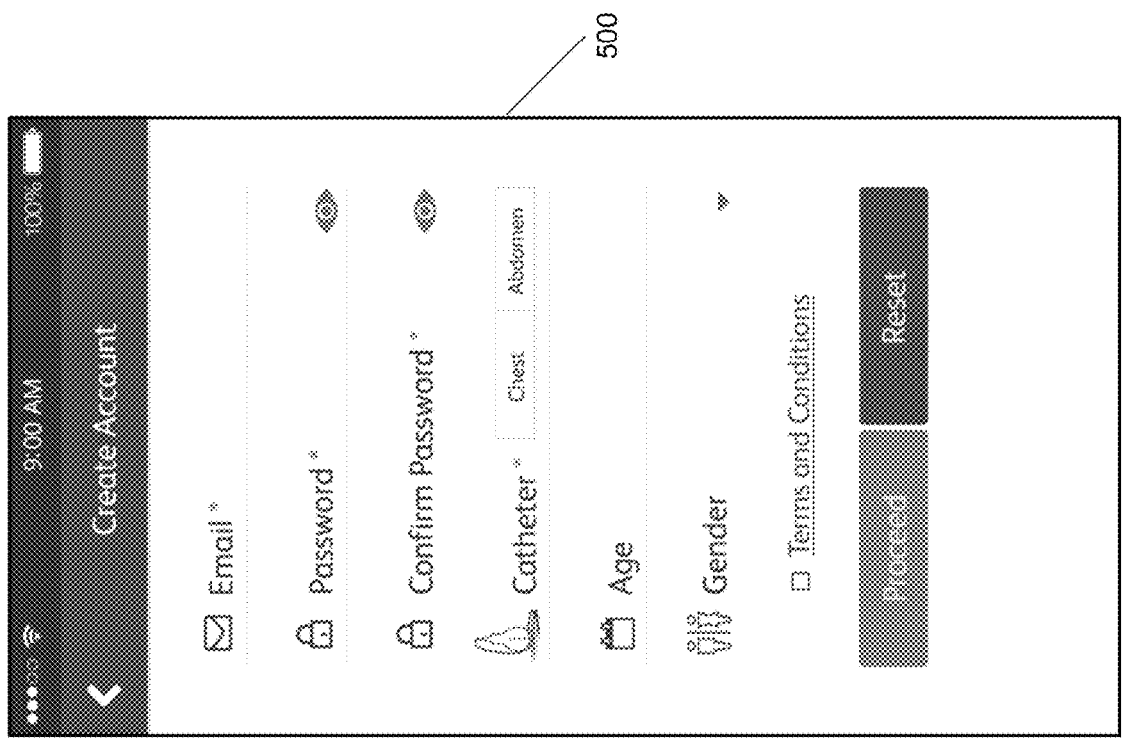
FIG. 5 shows an exemplary patient-side create account page of a patient-side user interface.

Another embodiment of a patient page is described with reference to FIG. 5. FIG. 5 depicts page 500, which is a create account page. Page 500 is configured to allow a patient-side user to create an account associated with system 200. Page 500 is configured to prompt a user to input a username (such as an e-mail address) and a password, and patient device 201a is configured to associate the entered username with the password within system 200. Page 500 is further configured to prompt a user to input other information about the patient associated with the created account, such as the type of catheter used by the patient, the age of the patient, and the gender of the patient, and patient device 201a is configured to then associate that entered information about the patient with the created account within system 200. Page 500 may be reached upon the user selecting the "Create Account" selectable link of page 400.

Figure 6A:
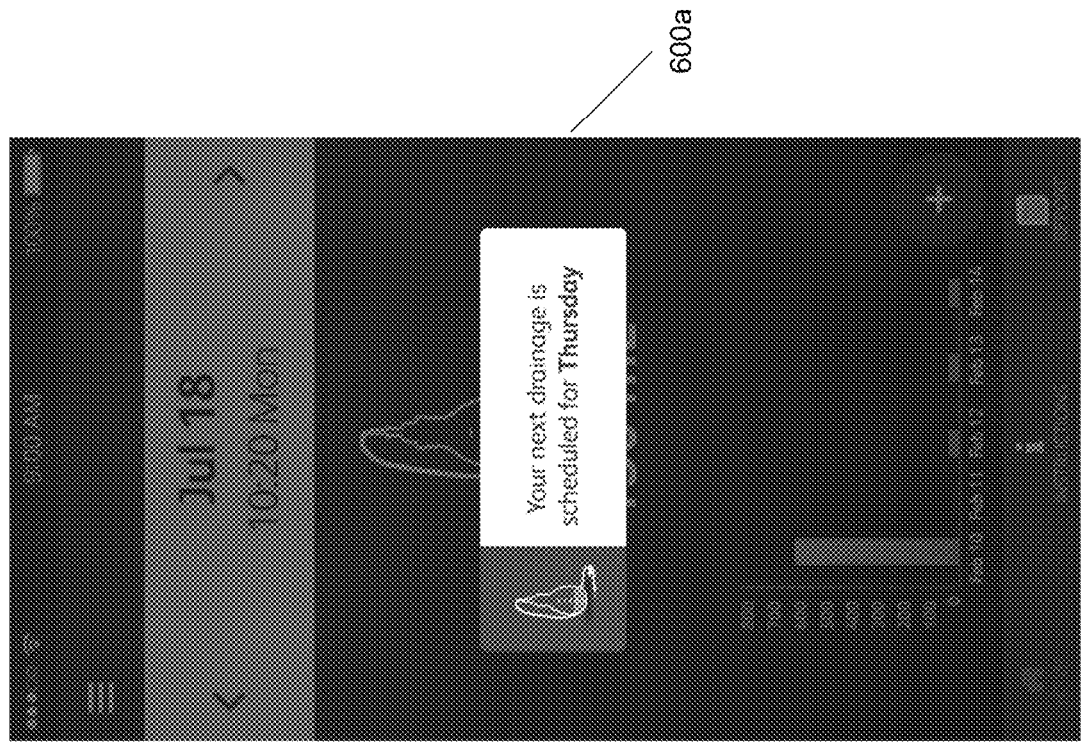
FIGS. 6A, 6B, and 6C show an exemplary patient dashboard page of a patient-side user interface.
Figure 6B:
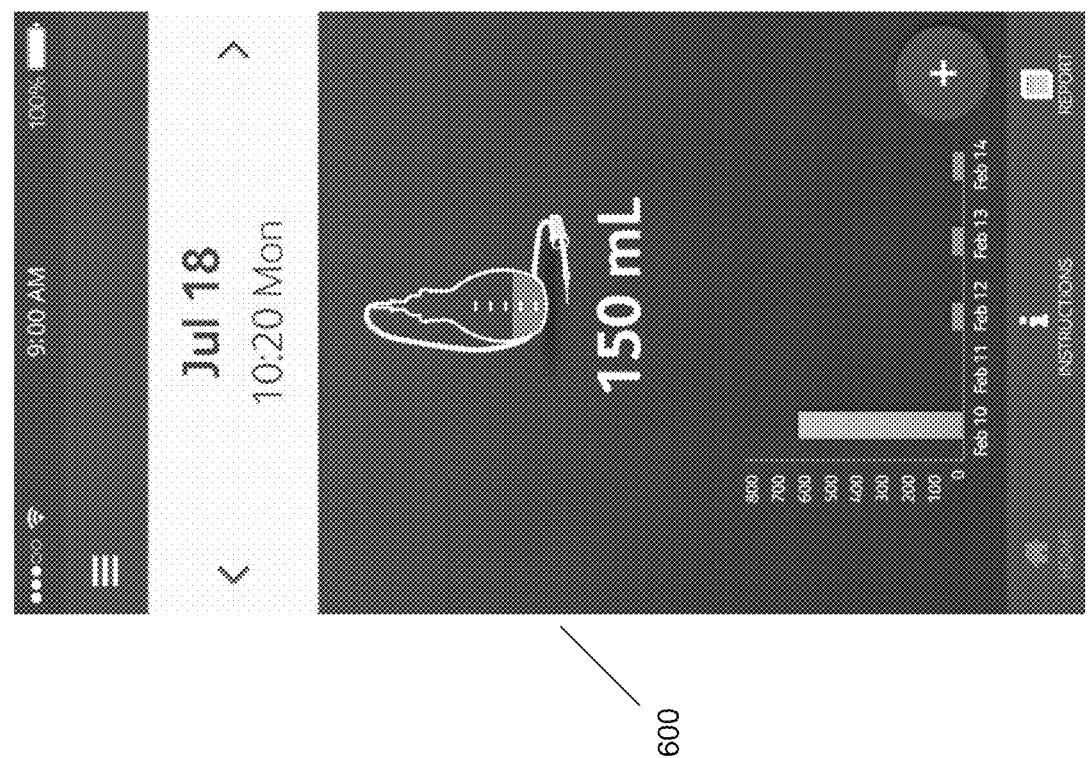
Figure 6C:
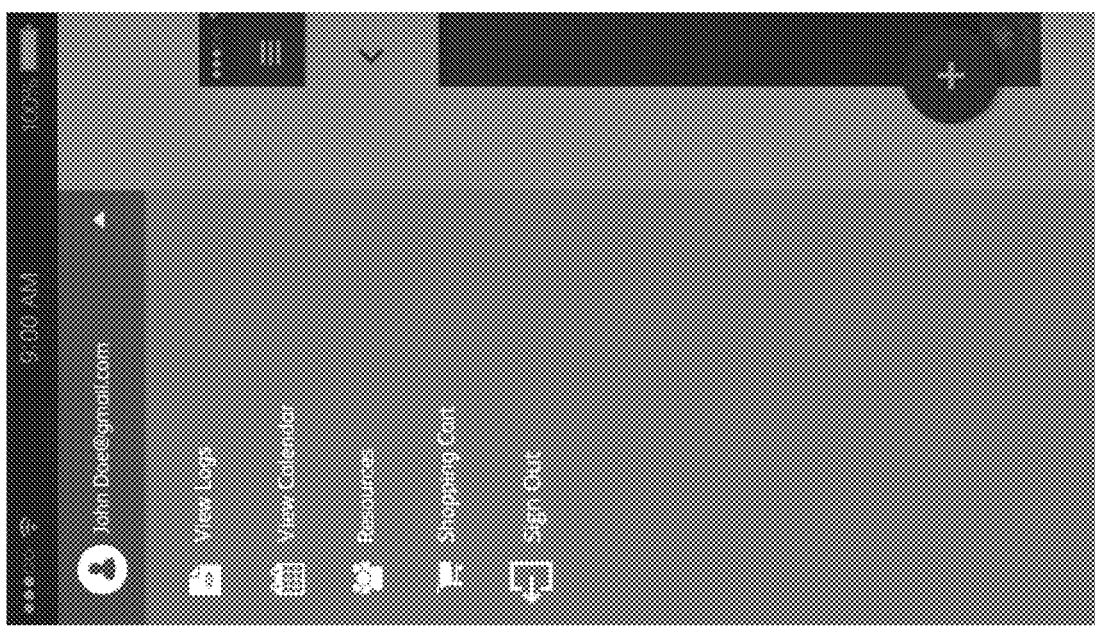

Another embodiment of a patient page is described with reference to FIGS. 6A-6C. FIGS. 6A-6C depict page 600, which is a patient dashboard that may be automatically reached after the user inputs a recognized username and password into page 400. Page 600 is configured to display information about the patient who is associated with the recognized username and password. Page 600 is configured to display recent drainage volumes input by the patient, as depicted in FIG. 6A. Page 600 is further configured to display a message 600a indicating the patient's next scheduled drainage. The message may be a pop-up message, as depicted in FIG. 6B. Patient device 201a may be configured to display page 600 based upon previously entered catheter use data, such as the patient's prescribed drainage schedule and/or a historical log of the patient's input catheter use data. Page 600 is further configured to display a plurality of selectable links each configured to display another of the exemplary pages of FIGS. 4-25 upon selection by the user. Page 600 may be configured to display some of the plurality of selectable links through a drop-down menu 600b displayed to the user by interacting with a button, as depicted in FIG. 6C.

Figure 7:
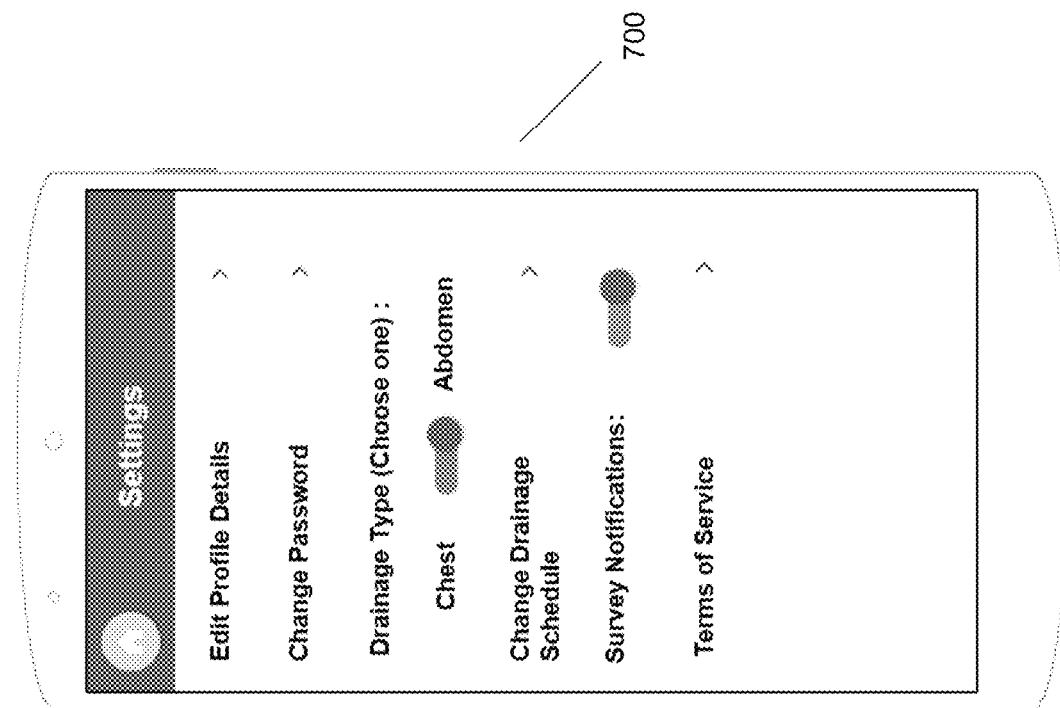
FIG. 7 shows an exemplary settings page of a patient-side user interface.

Another embodiment of a patient page is described with reference to FIG. 7. FIG. 7 depicts page 700, which is a settings screen that may be reached upon the user selecting a selectable "Settings" link (not shown) of page 600. Page 700 is configured to display interactive input elements that allow the user to input catheter use information including drainage type and drainage schedule settings.

Figure 8:
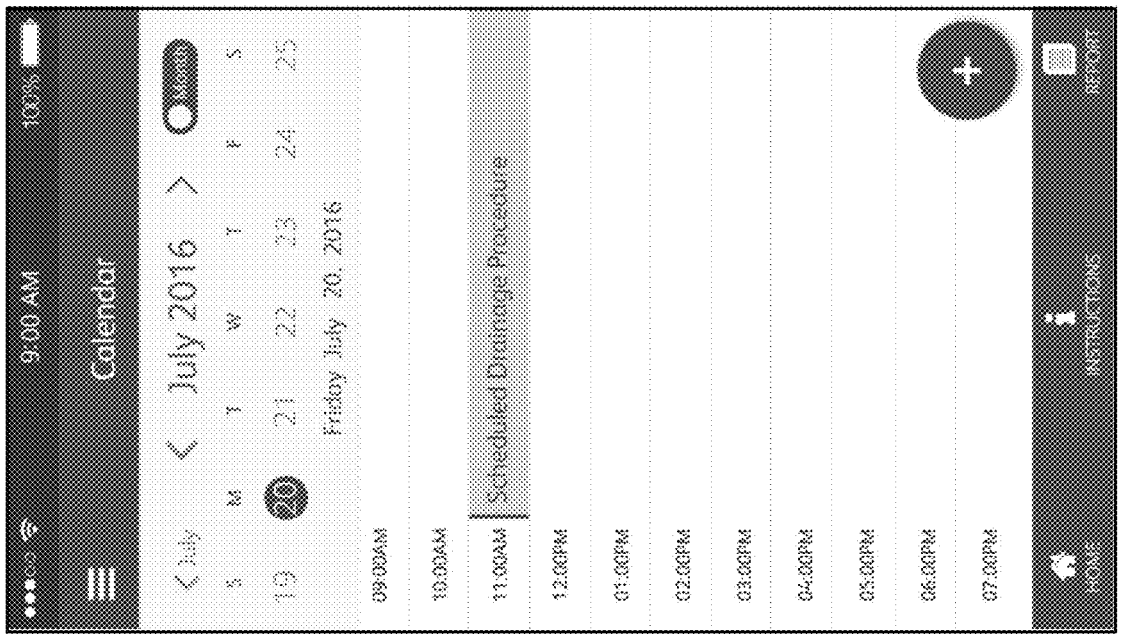
FIG. 8 shows an exemplary daily drainage schedule page of a patient-side user interface.

Another embodiment of a patient page is described with reference to FIG. 8. FIG. 8 depicts page 800, which is a daily drainage schedule screen configured to inform the user of the patient's next scheduled drainage. Page 800 may be reached upon the user selecting the "View Calendar" selectable link of page 600 and choosing the "Day" selectable link (not shown).

Figure 9:
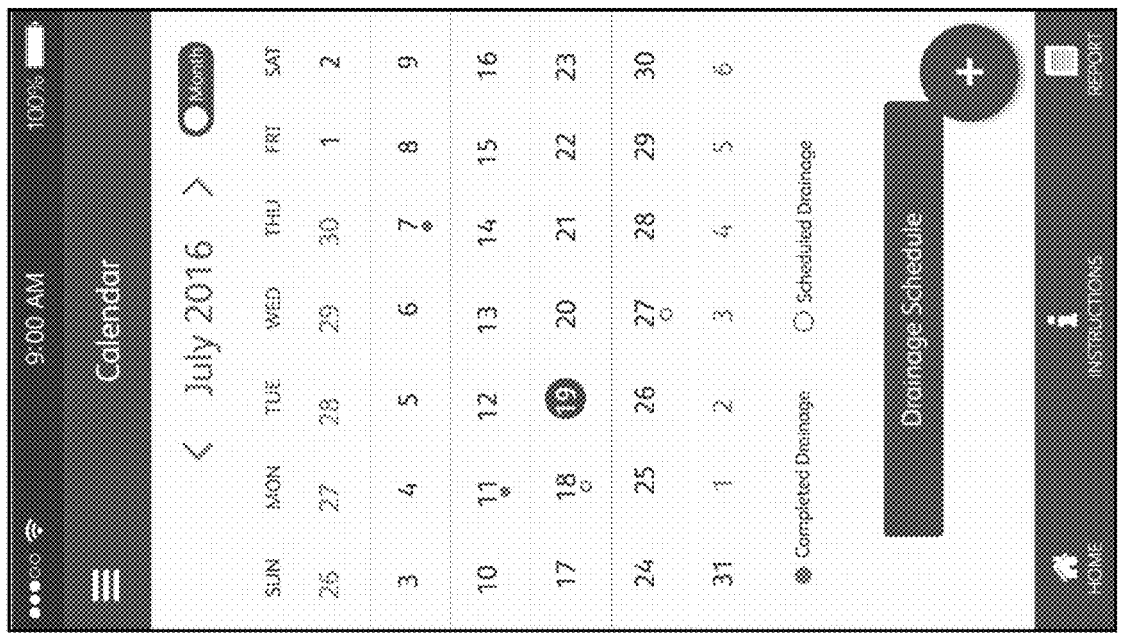
FIG. 9 shows an exemplary monthly drainage schedule page of a patient-side user interface.

Another embodiment of a patient page is described with reference to FIG. 9. FIG. 9 depicts page 900, which is a monthly drainage schedule screen configured to inform the user of scheduled drainages in a month and to allow the user to add an entry of catheter use information in association with a given day via various interactive input elements. Page 900 may be reached upon the user selecting the "View Calendar" selectable link of page 600 and choosing the "Month" selectable link (not shown).

Figure 10A:
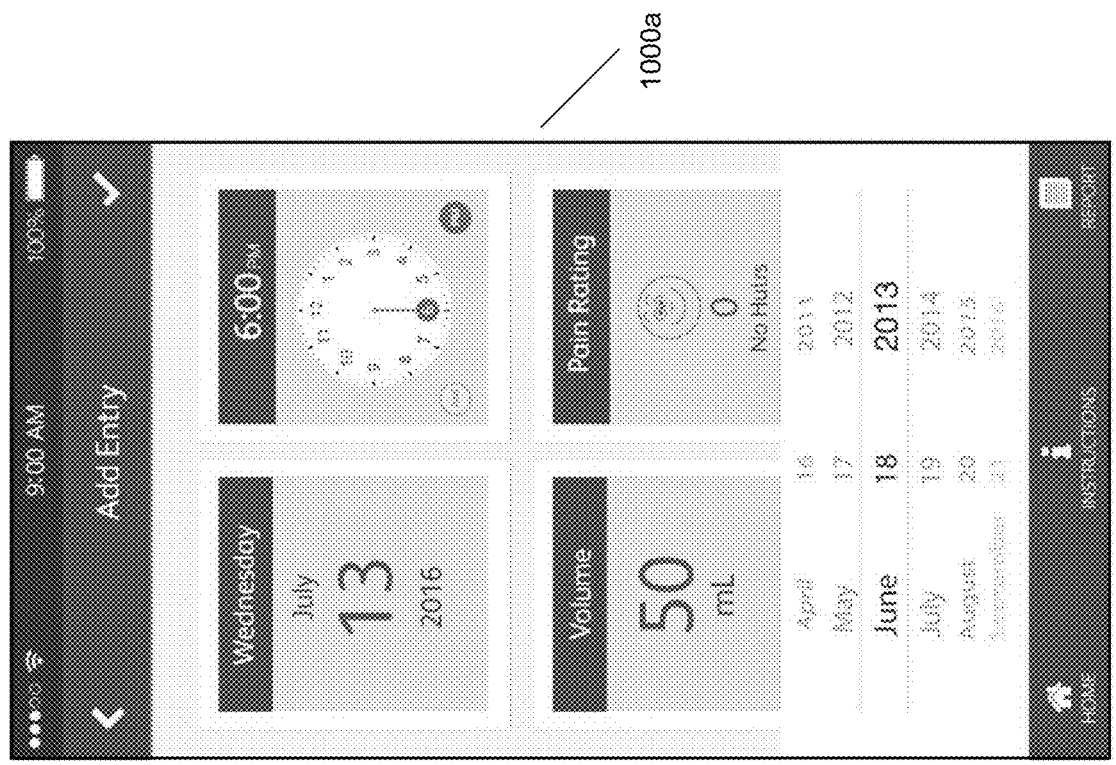
Figure 10B:
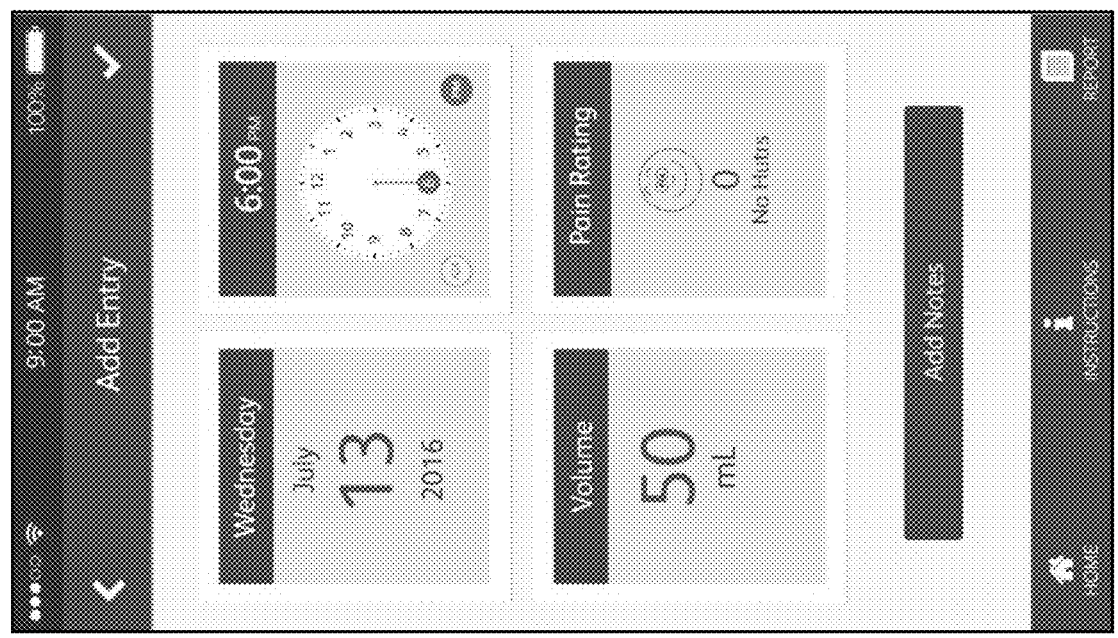
Figure 10E:
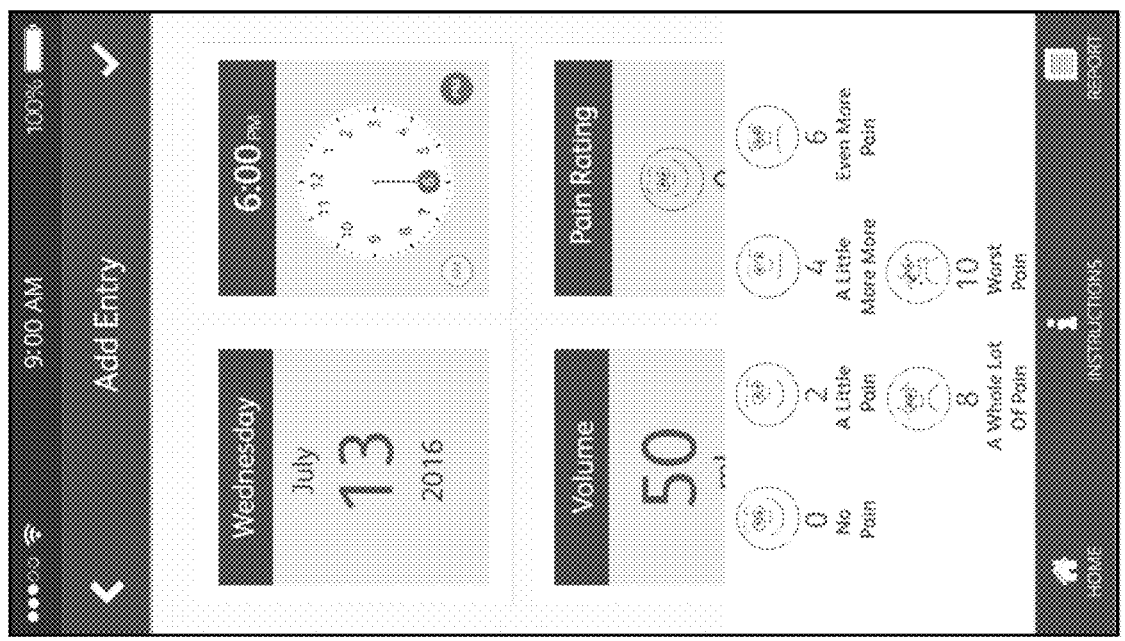

Another embodiment of a patient page is described with reference to FIGS. 10A-10E. FIGS. 10A-10E depict page 1000, which is an add entry page configured to prompt the user to input, through a variety of interactive input elements, various catheter use input information, including volume of drainage, date of drainage, time of drainage, patient discomfort level, and drainage details. Page 1000 may be reached upon selecting the Add Entry (i.e. "+") selectable link of pages 600, 800, 900, 1400, 2100, and/or 2200. Page 1000 may be configured to, in response to a user selecting an appropriate interactive input element, display a scroller that allows the user to input catheter use information associated with the respective interactive input element. For example, FIG. 10B depicts a scroller displayed by page 1000 in configuration 1000a in response to a user selecting the date of drainage interactive input element. FIG. 10C depicts a scroller displayed by page 1000 in configuration 1000b in response to a user selecting the time of drainage interactive input element. FIG. 10D depicts a scroller displayed by page 1000 in configuration 1000c in response to a user selecting the drainage volume interactive input element. FIG. 10E depicts a pop-up interface displayed by page 1000 in configuration 1000d in response to a user selecting the pain rating interactive input element, which is configured for a user to select an appropriate pain rating. Patient device 201a is configured to associate the catheter use information input through page 1000 with a catheter use information entry and with the patient.

Figure 11A:
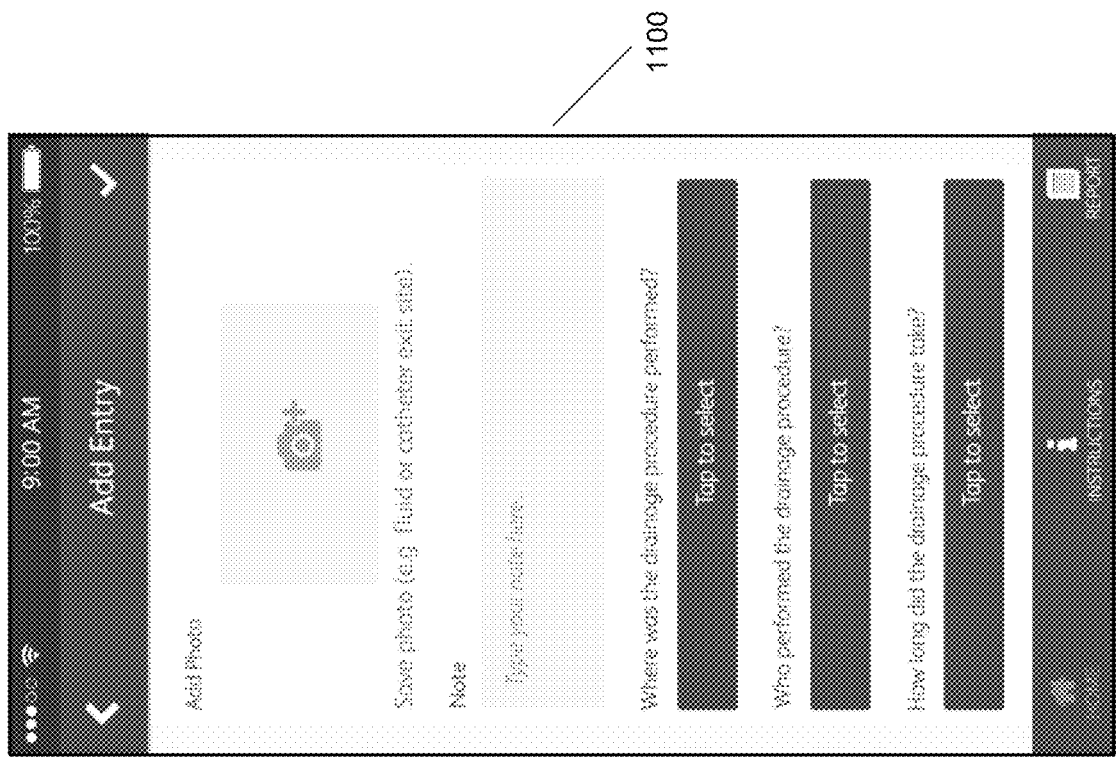
FIGS. 11A, 11B, and 11C show an exemplary catheter use information input page of a patient-side user interface.
Figure 11C:
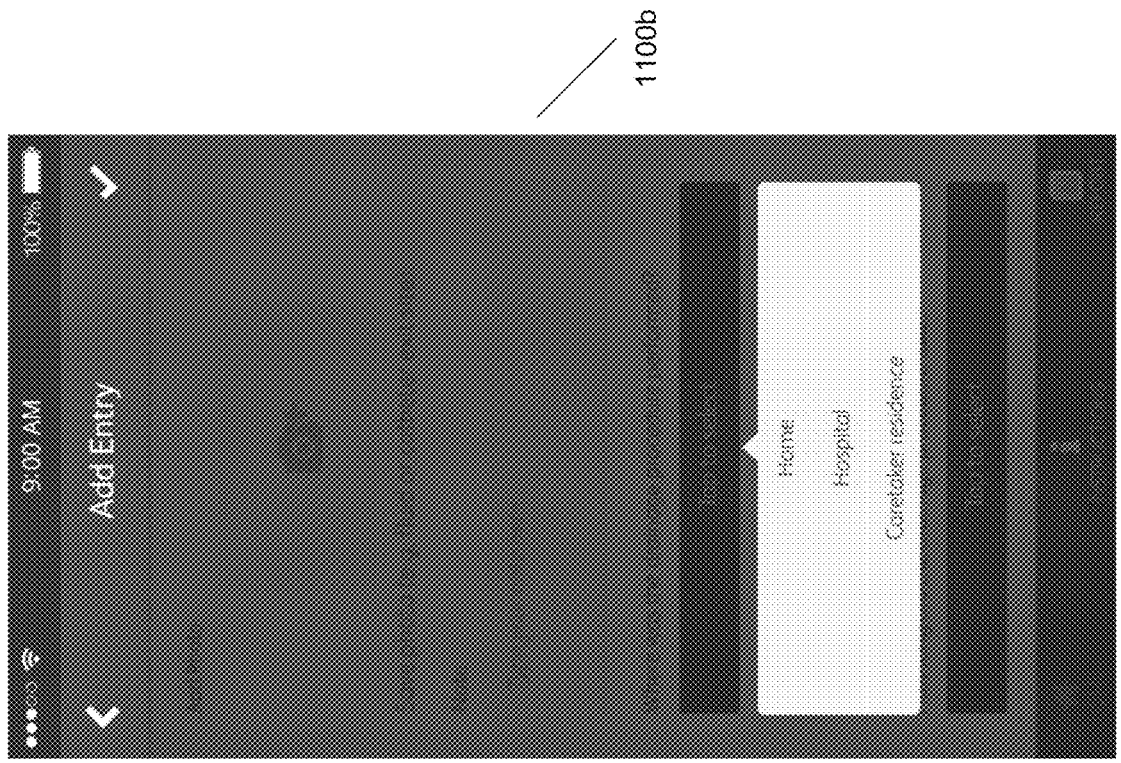
Figure 11B:

Another embodiment of a patient page is described with reference to FIGS. 11A-11C. FIGS. 11A-11C depict page 1100, which is a catheter use information input screen configured to prompt the user to input a variety of catheter use information using a plurality of interactive input elements. Page 1100 further allows the user to upload a picture, such as a picture of the used drainage bottle and its contents, or a picture of the patient's catheter exit site. Page 1100 may be configured to display a pop-up menu in response to a user selecting the "Add Photo" selectable link depicted in FIG. 11A. A pop-up menu configuration 1100a is depicted in FIG. 11B, and may include a plurality of selectable links that allow the user to choose an image already stored on patient device 201a, capture a new image using an image capture sensor of device 201a, or delete an image from device 201a. Page 1100 is further configured for the user to input notes to associate with a catheter use information entry. Page 1100 is further configured to allow the user to input additional information to store in association with a catheter use information entry. For example, page 1100 is configured to prompt a user to input information about where the drainage procedure was performed, who performed the drainage procedure, and how long the drainage procedure took. Page 1100 may be configured to prompt the user by displaying a drop-down menu configuration 1100b when a user selects a selectable link on page 1100, as depicted in FIG. 11C. Page 1100 may further be configured to prompt a user to indicate whether the patient is experiencing shortness of breath, coughing, chest discomfort, and excessive saliva. Page 1100 may be reached by a user selecting the "Add Notes" selectable link of page 1000.

Patient device 201a may be configured to receive a picture that has been uploaded to patient device 201a, for example using page 1100, and to perform image analysis on the uploaded picture. The picture may be of the patient's used drainage bottle and its contents, or of the patient's catheter exit site.

In an exemplary image analysis algorithm, patient device 201a may be configured to perform image analysis on an uploaded picture of a used drainage bottle and its contents to determine changes in color of the fluid in the bottle, and to automatically display a medical personnel contact recommendation and/or contact the physician upon a determination that a predetermined change in color has occurred. For example, patient device 201a may be configured to extract a color signal from the image and/or a transparency signal from the image. Patient device 201a may be further configured to compare an extracted color signal and/or transparency signal from an uploaded image with one or more color signals and/or transparency signals from one or more previous images associated with that patient, and to determine a percentage change in color signal and/or transparency signal from the previous image(s) to the analyzed image. Patient device 201a may be further configured to determine whether the percentage change in color signal and/or transparency signal is greater than a predetermined percentage. Patient device 201a may be further configured to, upon determining that the percentage change is greater than the predetermined percentage, display a medical personnel contact recommendation, and/or automatically contact medical personnel with a message informing the medical personnel that the patient is exhibiting the predetermined percentage change in color signal and/or transparency signal.

In an exemplary image analysis algorithm, patient device 201a may be configured to compare an extracted color signal and/or transparency signal from an uploaded image of the used bottle and its contents with one or more color signals and/or transparency signals from an electronic library storing used bottle and bottle contents images associated with all patients associated with system 200. Patient device 201a may be further configured to determine whether a predetermined relationship exists between the extracted color signal and/or transparency signal from the uploaded image and the one or more color signals and/or transparency signals from the used bottle and bottle contents images in the electronic library. The electronic library may be on or accessible to server 202.

In an exemplary image analysis algorithm, patient device 201a may be configured to perform image analysis on an uploaded picture of the used bottle and its contents to automatically determine and log drainage volume. For example, patient device 201a may be configured to detect top and bottom edges of the used bottle and top and bottom edges of fluid in the bottle. Patient device 201a may be further configured to use the detected edges to determine a height of the bottle and a height of the fluid. Patient device 201a may be further configured to calculate a ratio of bottle height to fluid height. Patient device 201a may be further configured to compare the calculated ratio to a predetermined scale relating a plurality of volumes of fluid in a bottle to a plurality of respective ratios of bottle height to fluid height, and to thereby determine a volume the corresponds to the calculated ratio. Patient device 201a may be further configured to store the determined volume as a drainage volume in a historical log of the patient.

In an exemplary image analysis algorithm, patient device 201a may be configured to perform analysis on an uploaded picture of the patient's catheter exit site. For example, patient device 201a may be configured to extract a color signal from an uploaded image. Patient device 201a may be further configured to compare an extracted color signal from the uploaded image with one or more color signals from one or more previous images associated with that patient, and to determine a percentage change in color signal from the previous image(s) to the analyzed image. Patient device 201a may be further configured to determine whether the percentage change in color is greater than a predetermined percentage. Patient device 201a may be further configured to, upon determining that the percentage change is greater than the predetermined percentage, display a medical personnel contact recommendation, and/or automatically contact medical personnel with a message informing the medical personnel that the patient is exhibiting the predetermined percentage change in color signal and may be exhibiting an infection.

In an exemplary image analysis algorithm, patient device 201a may be configured to compare an extracted color signal from an uploaded image of the patient's catheter exit site with one or more color signals and/or transparency signals from an electronic library storing catheter exit site images associated with all patients associated with system 200. Patient device 201a may be further configured to determine whether a predetermined relationship exists between the extracted color signal from the uploaded image and the one or more color signals from the catheter exit site images in the electronic library. The electronic library may be on or accessible to server 202.

In an exemplary image analysis algorithm, patient device 201a may be configured to use an extracted color signal from an uploaded image of a patient's catheter exit site to determine a size of red area around the catheter exit site. Patient device 201a may determine the size of red area around the catheter exit site by detecting an edge between the red area and a non-red area surrounding the red area, defining that edge as the boundary of the red area, and calculating the area within the boundary. Patient device 201a may be further configured to compare the calculated red area with one or more red areas from one or more previous images of the patient's catheter exit site to determine a percentage change in red area from the previous image(s). Patient device 201a may be further configured to compare the determined percentage change to a predetermined threshold percentage change, and to display a medical personnel contact recommendation, and/or automatically contact medical personnel with a message informing the medical personnel that the patient is exhibiting the predetermined percentage change in red area and may be exhibiting an infection.

Figure 12:
FIG. 12 shows an exemplary catheter use information input page of a patient-side user interface.

Another embodiment of a patient page is described with reference to FIG. 12. FIG. 12 depicts page 1200, which is a catheter use information input screen configured to prompt the user to input a plurality of catheter use information. Page 1200 is configured to prompt the user to input whether the catheter site may be infected, whether pain is experienced, whether the patient drained more than 1000 mL, and whether the patient drained less than 50 mL three times in a row. In some embodiments, patient device may be configured to display a medical personnel contact recommendation when the user selects one or more of the interactive input elements of page 1200 that indicate that a user is experiencing the prompted-for conditions. In some embodiments, patient device 201a may be configured to automatically generate and transmit a signal to physician device 203 and/or nurse device 204 upon user selection of those interactive input elements. For example, patient device 201a may be configured to receive, via page 1200, an input from the user indicating that the patient has drained less than 50 mL for three consecutive drainages, and in response: (1) display a medical personnel contact recommendation; and/or (2) automatically provide a diagnosis that the patient may have achieved pleurodesis; and/or (3) automatically provide a signal informing the physician that the patient should come in for a follow up appointment.

Figure 13:
FIG. 13 shows an exemplary ambulation information input page of a patient-side user interface.

Another embodiment of a patient page is described with reference to FIG. 13. FIG. 13 depicts page 1300, which is an ambulation information input screen configured to prompt the user to input a description of the patient's ambulatory ability, and to receive the input using a plurality of selectable interactive input elements.

Figure 14A:
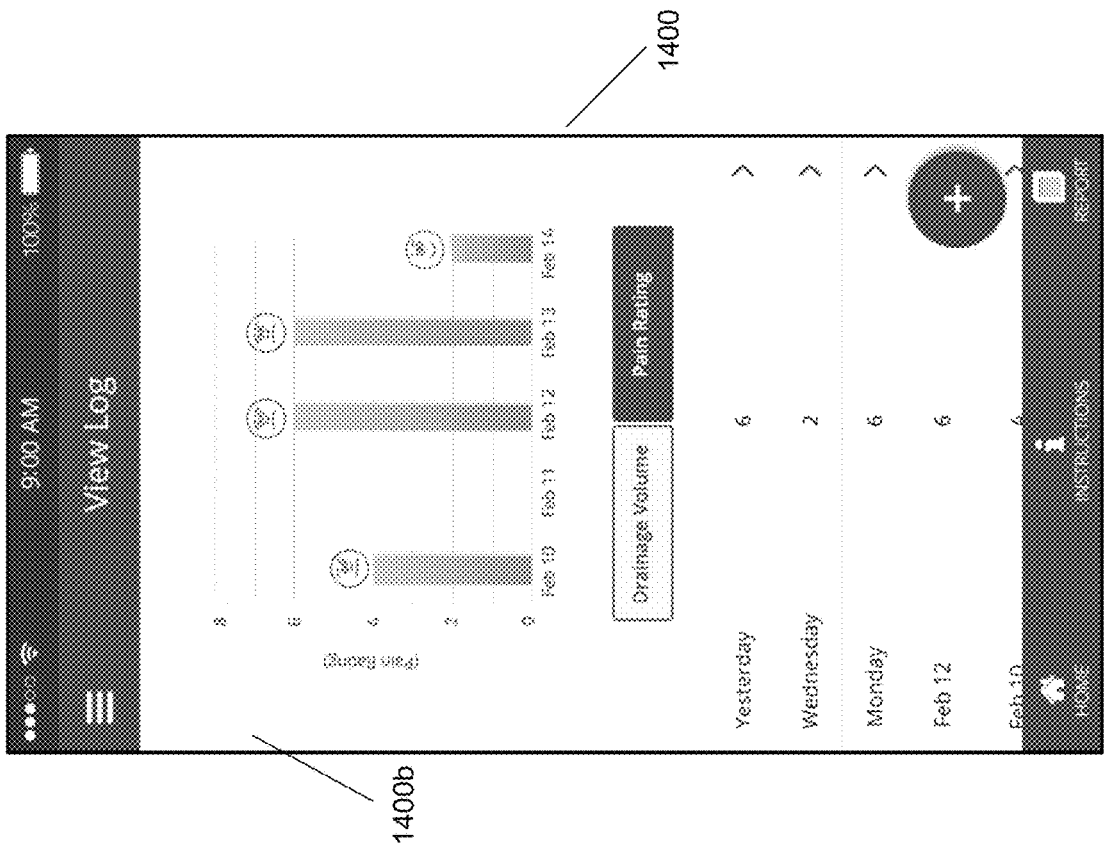
FIGS. 14A and 14B show an exemplary view log page of a patient-side user interface.
Figure 14B:
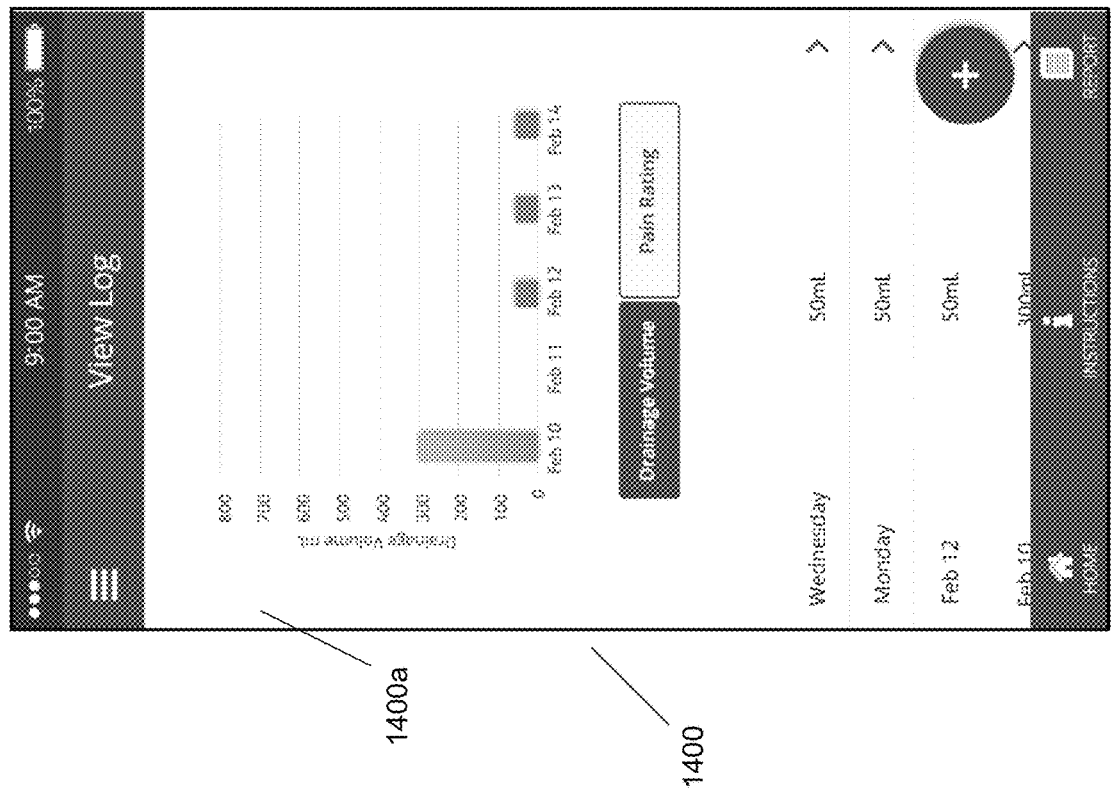

Another embodiment of a patient page is described with reference to FIGS. 14A-14B. FIGS. 14A-14B depict page 1400, which is a view log screen configured to display a historical log in a chart form depicting the drainage volume or discomfort level (e.g. pain rating) at various dates. The historical log of page 1400 may be generated by patient device 201a based upon catheter use information input through page 1000 and/or page 1100. Page 1400 also includes interactive input elements configured to allow the user to toggle from the historical log for drainage volume 1400a, depicted in FIG. 14A, to the historical log for discomfort level 1400b, depicted in FIG. 14B. Historical log for drainage volume 1400a may depict drainage volumes that are below a threshold level, such as 50 mL, in a manner distinct from drainage volumes not below that threshold level, for example by using a different color, as depicted in FIG. 14A. The bar charts of page 1400 shown in FIGS. 14A and 14B may be configured to scroll horizontally, such that information from additional dates can be displayed on the screen of patient device 201a. Additionally, the listing of logged data of page 1400 shown in FIGS. 14A and 14B below the bar charts may be configured to scroll vertically, such that information from additional dates can be displayed on the screen of patient device 201a. Page 1400 can be reached upon the user selecting the "View Logs" link of page 600.

Patient device 201a may be configured to automatically perform analysis upon data of a historical log in order to generate and/or display one or more patient diagnoses and/or medical personnel contact recommendations. For example, patient device 201a may be configured to execute an algorithm which analyzes a historical log, such as the historical log whose data is displayed by page 1400. The algorithm may monitor drainage volumes and/or patient discomfort levels over some number of consecutive days to determine a trend.

In an embodiment of an exemplary historical log analysis algorithm, patient device 201a may be configured to recognize when a historical log includes three consecutive days in which drainage of 50 mL or less of drainage is recorded, and to in response determine that the patient is exhibiting a pattern indicating they have achieved pleurodesis. Patient device 201a may be further configured to, in response to the determination that the patient is exhibiting a pattern indicating they have achieved pleurodesis, display a medical personnel contact recommendation to the user, and/or automatically contact medical personnel with a message informing the medical personnel of the diagnosis.

In an embodiment of an exemplary historical log analysis algorithm, patient device 201a may be configured to recognize that the patient's drainage has rapidly dropped from an amount within an expected range during one or more days to nearly zero drainage during one or more subsequent days, and to in response determine that the patient's catheter might be clogged. Patient device 201a may be further configured to, in response to a determination that the patient's catheter might be clogged, look up the patient's discomfort levels from the days with nearly zero drainage and compare them to a predetermined threshold. Patient device 201a may be further configured to, upon a determination that the patient's discomfort levels from those days are below a threshold, determine that the patient is not feeling well, and in response display a medical personnel contact recommendation to the user, and/or automatically contact medical personnel with a message informing the medical personnel that the patient's catheter may be clogged and that the patient should visit the medical personnel.

In an embodiment of an exemplary historical log analysis algorithm, patient device 201a may be configured to recognize that the patient's drainage has shown a trend of decreasing over some number of consecutive days, and has then substantially increased in a manner indicating that effusion has reoccurred. Patient device 201a may be configured to, upon a determination that effusion has reoccurred, display a medical personnel contact recommendation to the user, and/or automatically contact medical personnel with a message informing the medical personnel that effusion has reoccurred and to monitor the patient to determine the cause of the reoccurrence. For example, the message may suggest that the medical personnel perform ultrasound and/or X-ray imaging of the patient.

In an embodiment of an exemplary historical log analysis algorithm, patient device 201a may be configured to recognize when a historical log includes random drainage over some number of consecutive days. Patient device 201a may be further configured to determine that the patient's drainage has been random over the number of consecutive days by determining that the patient's drainage over the number of consecutive days does not exhibit a trend for which medical personnel should be contacted (e.g. pleurodesis has been achieved, potential catheter clog, effusion reoccurrence, etc.). Patient device 201a may be further configured to, upon a determination that the patient's drainage has been random over the consecutive number of days, display a message to the user to continue routine drainage, and/or automatically contact medical personnel with a message informing the medical personnel that the patient should continue routine drainage.

In an embodiment of an exemplary historical log analysis algorithm, patient device 201a may be configured to recognize when a historical log includes a trend of increasing quality of life. For example, patient device 201a may be configured to recognize a trend of increasing quality of life when a historical log includes a trend of decreasing discomfort levels. Patient device 201a may be further configured to, upon determining that the patient's quality of life has been increasing (e.g. when the patient's discomfort levels have been decreasing), display a medical personnel contact recommendation to the user, and/or automatically contact medical personnel with a message informing the medical personnel that the patient's quality of life is improving and to consider bringing in the patient and performing more aggressive chemotherapy treatment.

In an embodiment of an exemplary historical log analysis algorithm, patient device 201a may be configured to recognize when a historical log includes a trend of decreasing quality of life. For example, patient device 201a may be configured to recognize a trend of decreasing quality of life when a historical log includes a trend of increasing discomfort levels. Patient device 201a may be further configured to, upon determining that the patient's quality of life has been decreasing (e.g. when the patient's discomfort levels have been increasing), display a medical personnel contact recommendation to the user, and/or automatically contact medical personnel with a message informing the medical personnel that the patient's quality of life is decreasing and to consider bringing in the patient and adjusting chemotherapy treatment.

In an embodiment of an exemplary historical log analysis algorithm, patient device 201a may be configured to automatically monitor trends in a patient's catheter use information and/or catheter management information and automatically adjust the patient's drainage schedule based thereon. For example, for ascites patients, resolution of fluid build-up may not be an expected outcome, so a goal may be to achieve steady states for patient quality of life (or comfort), food intake, and fluid drainage volumes. Patient device 201a may be configured to recognize that a patient's historical log shows a fluctuation in quality of life (e.g. discomfort level), appetite, and/or drainage volumes from day to day. An exemplary fluctuation may be defined as a series of daily values that alternate from relatively high to relatively low from day to day. Patient device 201a may be configured to adjust the patient's drainage schedule in response to recognizing the fluctuation in quality of life, appetite, and/or drainage volume. Patient device 201a may be configured to adjust the patient's drainage schedule by displaying one or more prompts configured to cause more frequent fluid drainage of the patient. Patient device 201a may be configured to automatically monitor the patient's quality of life, appetite, and/or drainage volume after the patient's drainage schedule has been adjusted, and to further adjust the patient's drainage schedule until monitored quality of life, appetite, and/or drainage volumes reach respective optimized levels. Optimized levels may be defined as steady state levels.

Figures 15, 16:
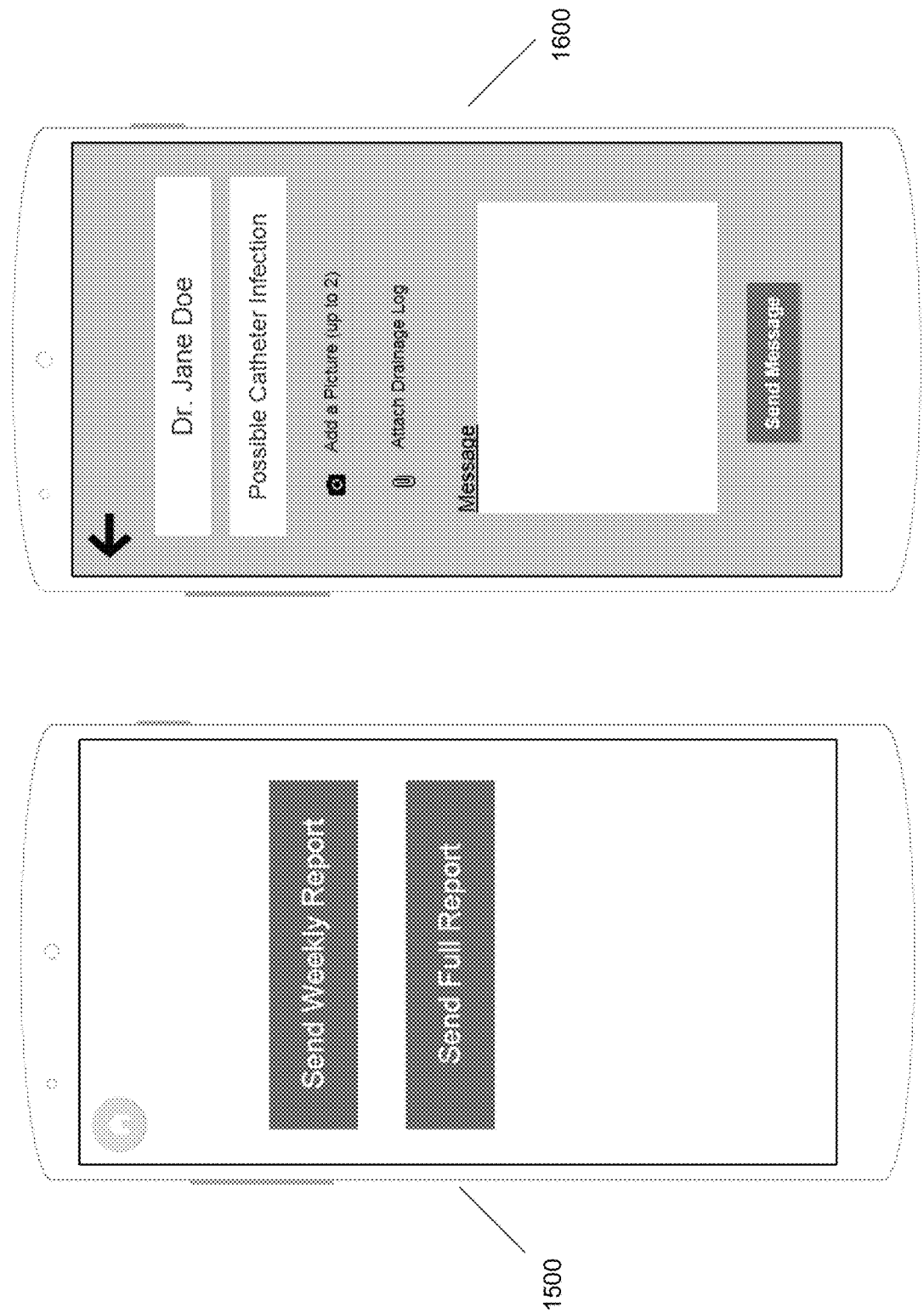
FIG. 15 shows an exemplary send report page of a patient-side user interface.
FIG. 16 shows an exemplary report page of a patient-side user interface.

Another embodiment of a patient page is described with reference to FIG. 15. FIG. 15 depicts page 1500, which is a send report screen including interactive input elements configured to allow the user to send a weekly report or a full report from patient device 201a to server 202, physician device 203, and/or nurse device 204. Page 1500 can be reached by a user selecting the "Report" selectable link of pages 800, 900, 1000, 1100, and/or 1400.

Another embodiment of a patient page is described with reference to FIG. 16. FIG. 16 depicts page 1600, which is a report screen. Page 1600 includes a plurality of interactive input elements configured to allow the user to generate and send a report file by selecting a recipient, adding pictures and drainage log files, inputting a message, and selecting a send link. Page 1600 may be reached upon selecting an interactive input element on page 1500. Patient device 201a may be configured to send the report file to physician device 203 and/or nurse device 204.

Figure 17:
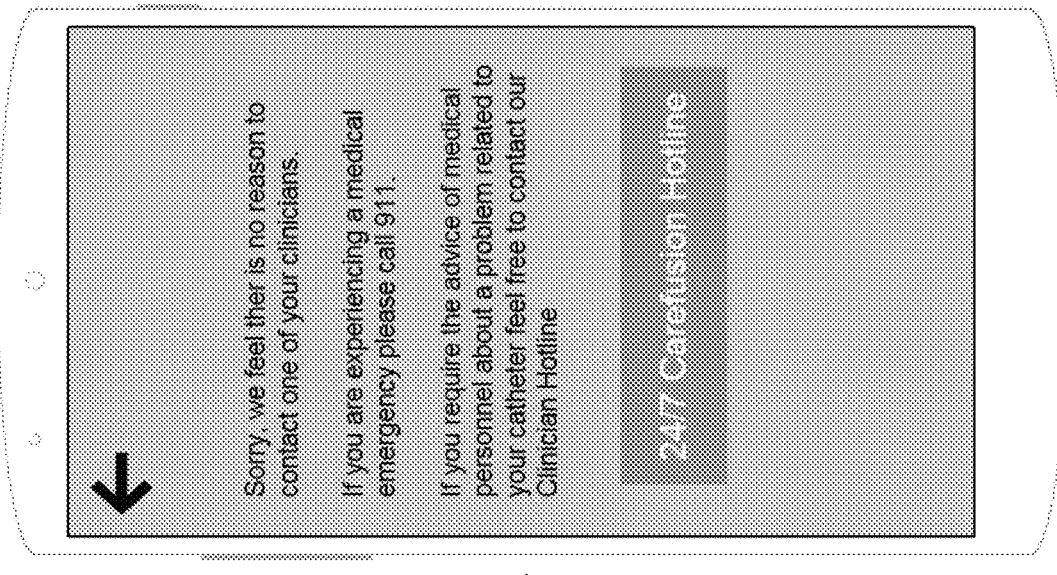
FIG. 17 shows an exemplary medical personnel contact recommendation page of a patient-side user interface.

Another embodiment of a patient page is described with reference to FIG. 17. FIG. 17 depicts page 1700, which is a medical personnel contact recommendation screen. Patient device 201a may be configured to display a medical personnel contact recommendation screen upon a user selecting one or more of the interactive input elements shown on page 1200 that confirm that the patient is experiencing the conditions associated therewith. In some embodiments, the displayed medical personnel contact recommendation may simply prompt the user to contact medical personnel. Page 1700 is an example of a medical personnel contact recommendation screen that may be displayed if none of the interactive input elements of page 1200 are selected by the user. Page 1700 further includes a link to contact a hotline associated with using the catheter to drain fluid from the patient. The link may be configured to cause patient device 201a to make a telephone call to the hotline upon the user selecting the link.

Figure 18:
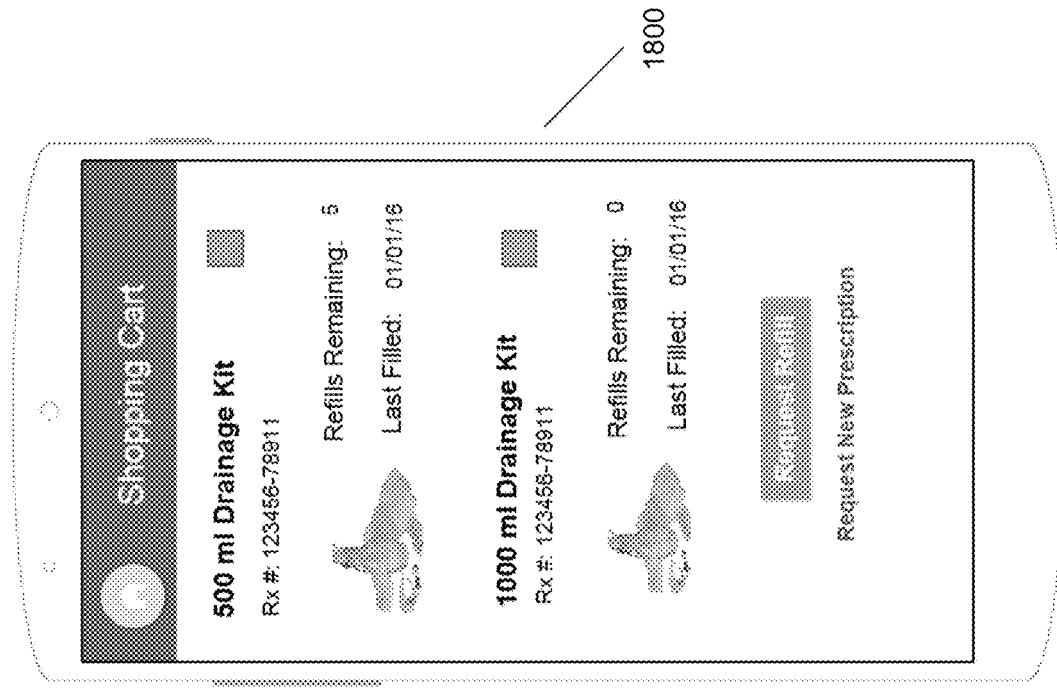
FIG. 18 shows an exemplary shopping cart page of a patient-side user interface.

Another embodiment of a patient page is described with reference to FIG. 18. FIG. 18 depicts page 1800, which is a shopping cart screen. Page 1800 includes a plurality of interactive input elements configured to allow the user to select components to use a catheter to drain fluid from a patient, and to submit a request to order the selected components. Page 1800 can be reached upon the user selecting the selectable shopping cart link of page 600. Patient device 201a may be configured to display page 1800 based upon catheter use information. For example, patient device 201a may execute an algorithm that receives from physician device 203 a number of refills for a patient, subtracts a refill from that number each time a user submits a request for a refill using page 1800, and displays the updated refills remaining on page 1800.

Figure 19:
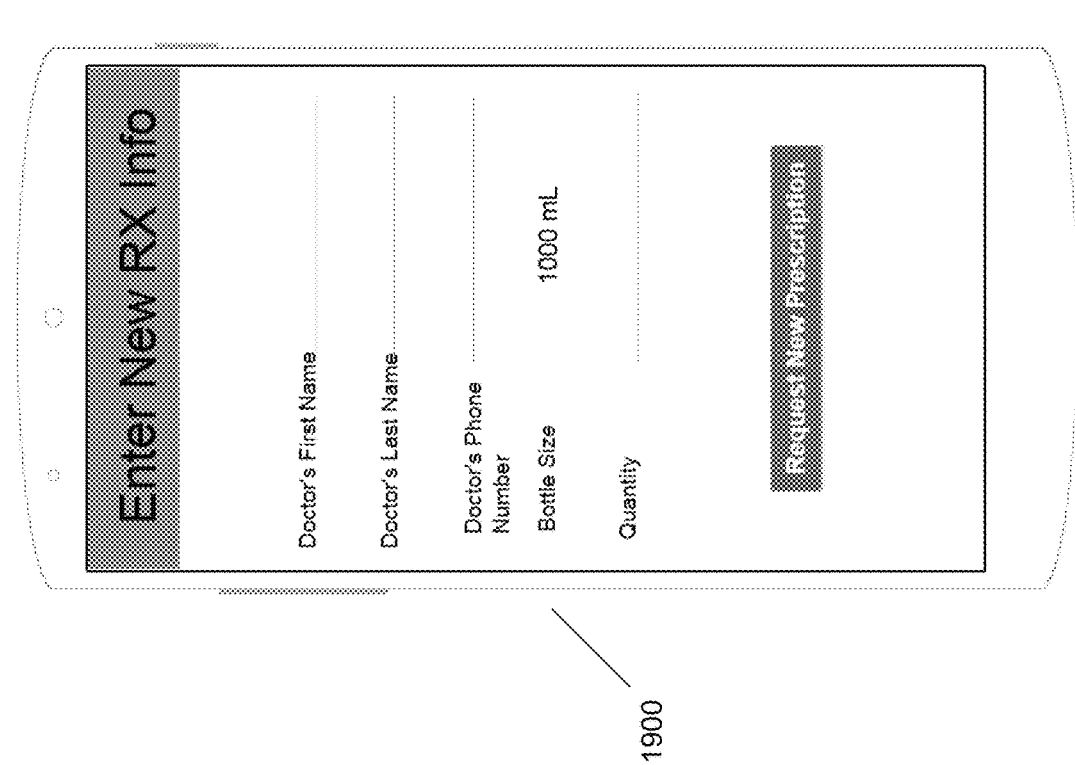
FIG. 19 shows an exemplary request prescription page of a patient-side user interface.

Another embodiment of a patient page is described with reference to FIG. 19. FIG. 19 depicts page 1900, which is a request prescription screen. Page 1900 includes a plurality of interactive input elements allowing the user to input information about the patient's doctor and required components of using the catheter to drain fluid, and to submit a request for a new prescription. Page 1900 can be reached upon the user selecting the "Request New Prescription" link of page 1800. Patient device 201a may be configured to send the request for a new prescription to server 202, physician device 203, and/or nurse device 204 upon selection of the "Request New Prescription" link of page 1900.

Figure 20:
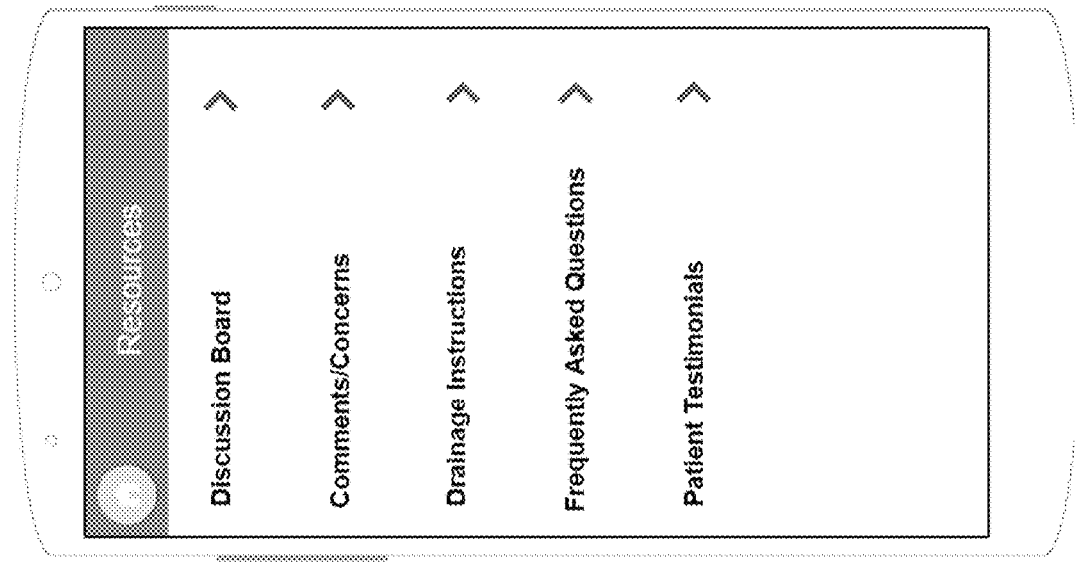
FIG. 20 shows an exemplary resources page of a patient-side user interface.

Another embodiment of a patient page is described with reference to FIG. 20. FIG. 20 depicts page 2000, which is a resources screen. Page 2000 includes a plurality of interactive input elements configured to allow the user to select sources of instructions for and background information about using the catheter to drain fluid. Page 2000 can be reached upon the user selecting the resources link of page 600.

Figure 21:
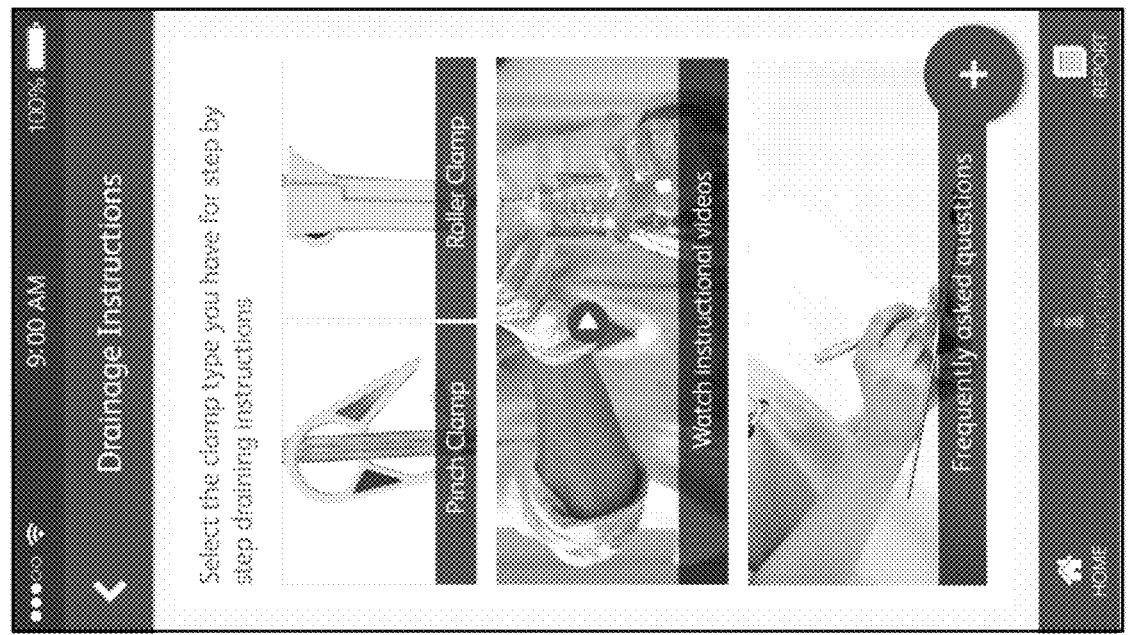
FIG. 21 shows an exemplary instructions selection page of a patient-side user interface.
Figures 23A, 23B:
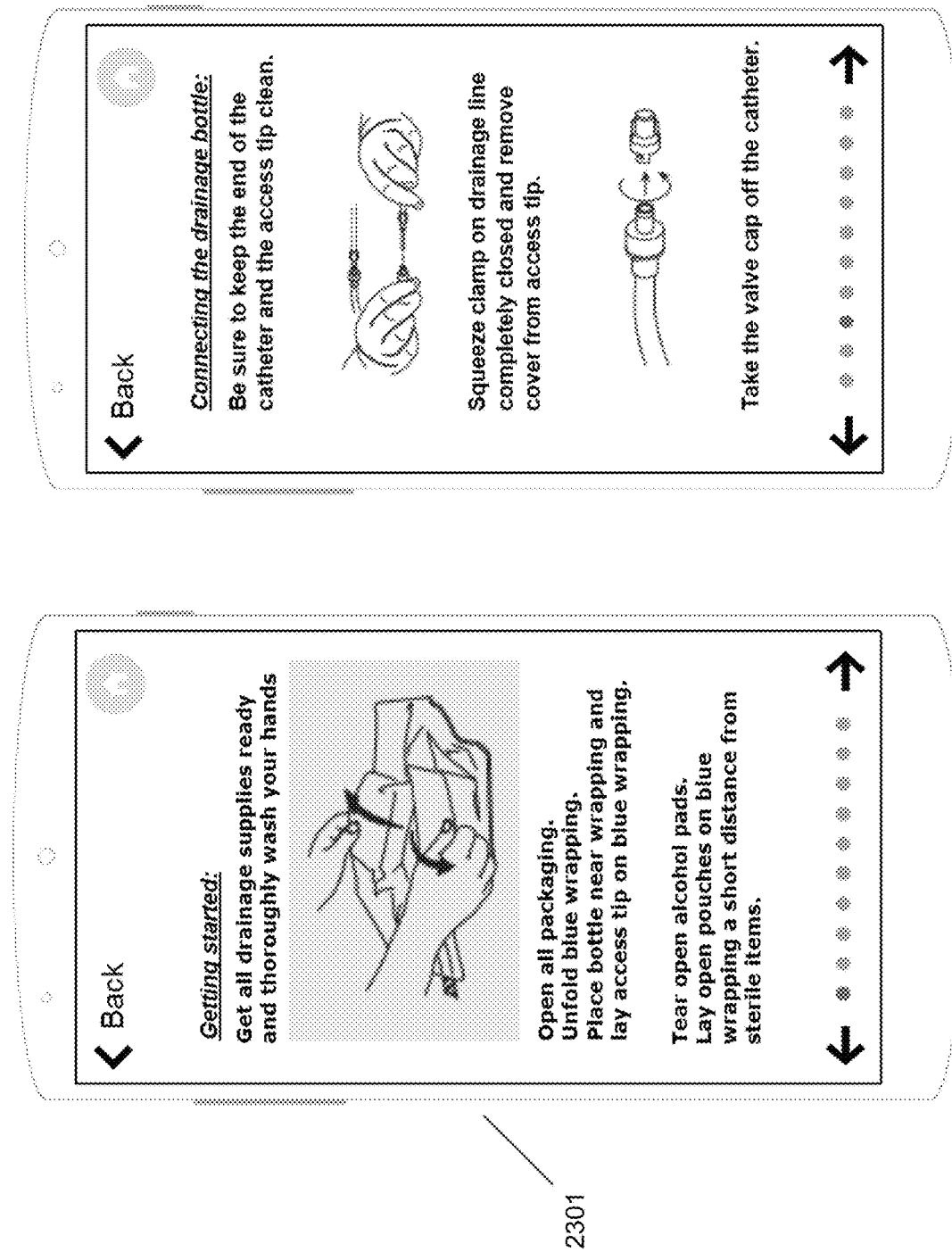
FIGS. 23A, 23B, 23C, and 23D respectively show different exemplary instructions pages of a patient-side user interface.
Figures 23C, 23D:
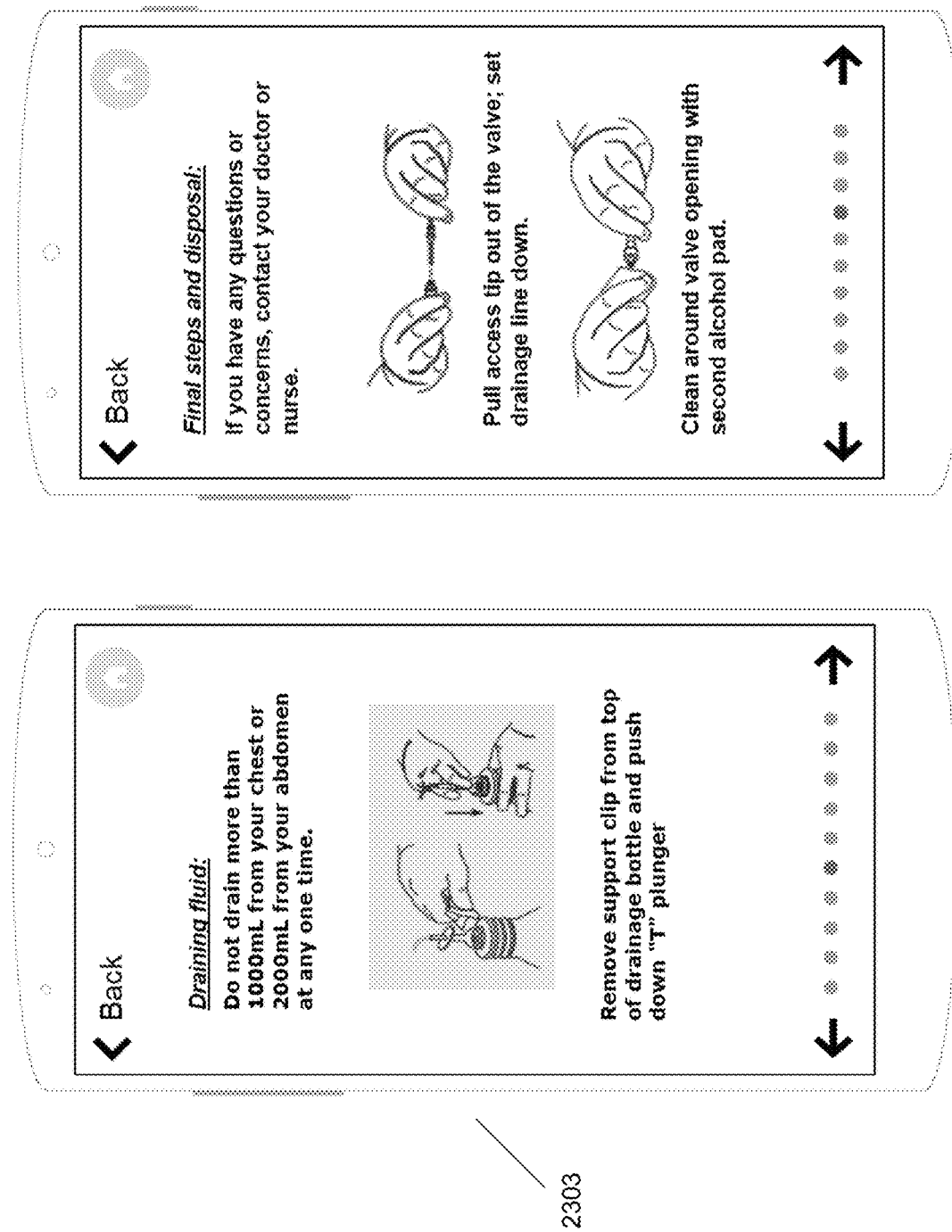

Another embodiment of a patient page is described with reference to FIG. 21. FIG. 21 depicts page 2100, which is an instructions selection page. Page 2100 includes a plurality of interactive input elements configured to prompt the user to input catheter use information about the clamp type, prompt the user to select from instructional videos, and prompt the user to select a link to frequently asked questions. Page 2100 can be reached upon the user selecting the "Drainage Instructions" link of page 2000.

Figure 22:
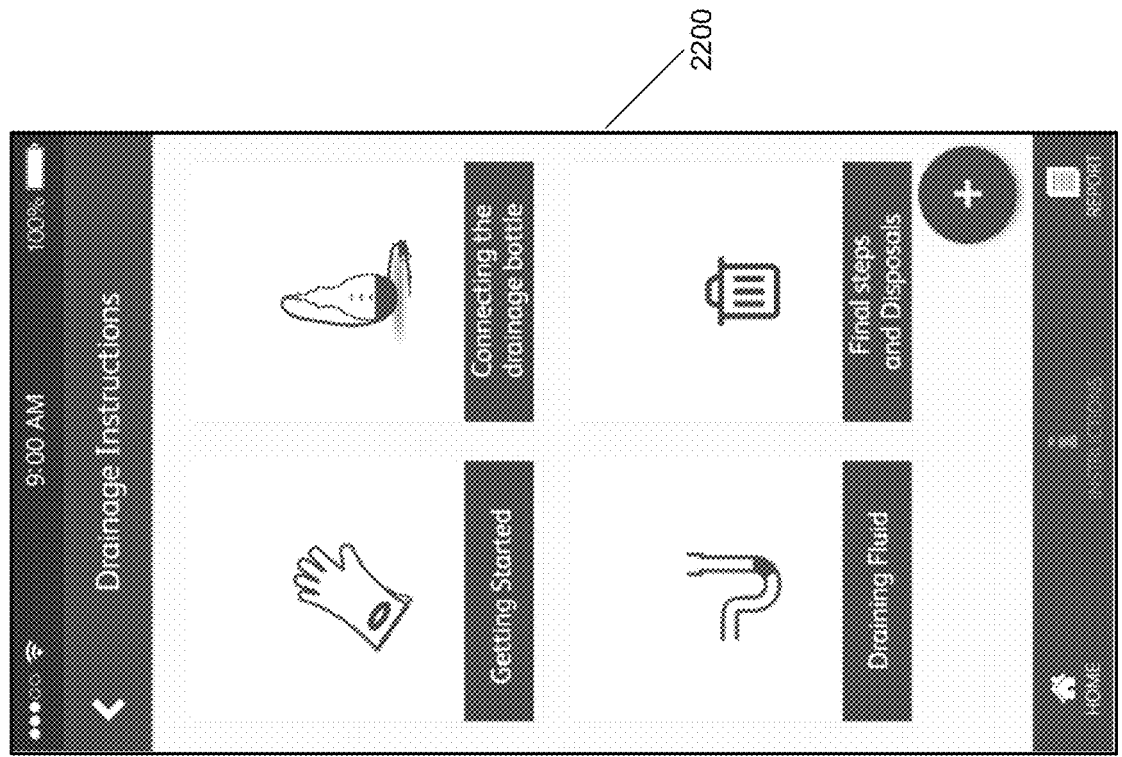
FIG. 22 shows an exemplary detailed instructions selection page of a patient-side user interface.

Another embodiment of a patient page is described with reference to FIG. 22. FIG. 22 depicts page 2200, which is a detailed instructions selection screen. Page 2200 includes a plurality of interactive input elements configured to prompt the user to select a relevant set of instructions for a particular part of the drainage process. Page 2200 can be reached by selecting the appropriate clamp type link of page 2100.

Another embodiment of a patient page is described with reference to FIGS. 23A, 23B, 23C, and 23D. FIGS. 23A, 23B, 23C, and 23D respectively depict pages 2301, 2302, 2303, and 2304, which are respectively instructions screens for: preparing to drain; connecting the drainage bottle; draining fluid; and finishing draining. Pages 2301, 2302, 2303, and 2304 can respectively be reached upon the user selecting the corresponding selectable link from page 2200.

Figure 24:
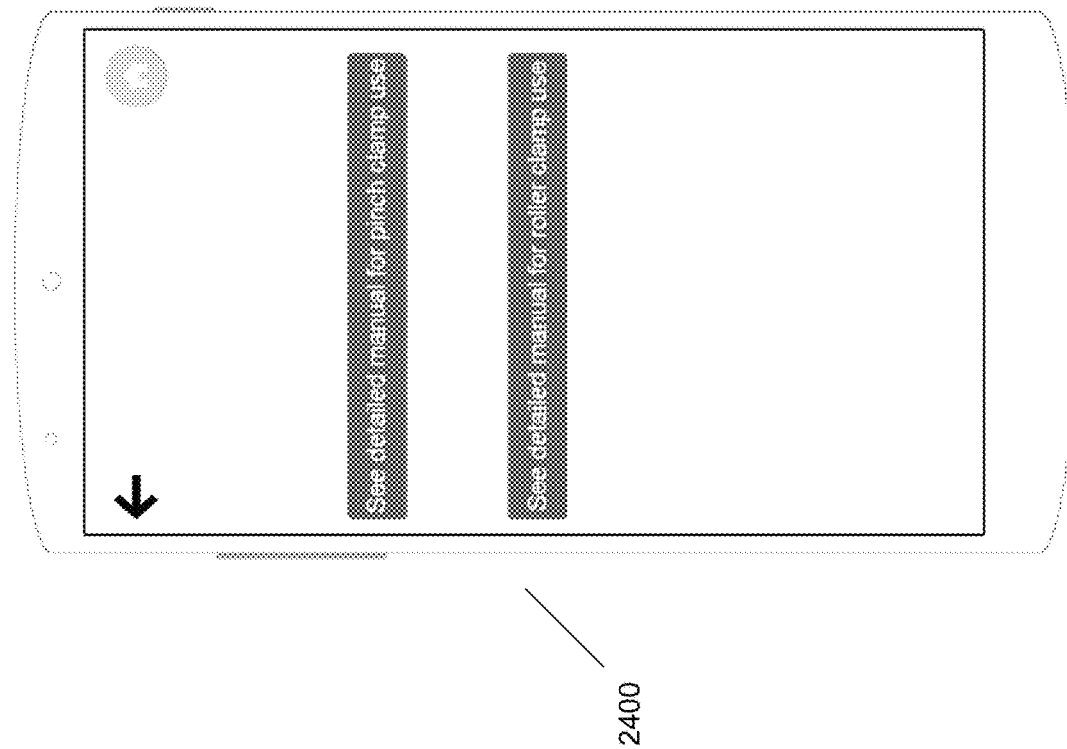
FIG. 24 shows an exemplary detailed manual selection page of a patient-side user interface.

Another embodiment of a patient page is described with reference to FIG. 24. FIG. 24 depicts page 2400, which depicts a detailed manual selection screen including selectable links providing the user access to detailed manuals according to clamp type. Page 2400 can be reached upon the user selecting the "View detailed instructions" link of page 2100.

Figure 25:
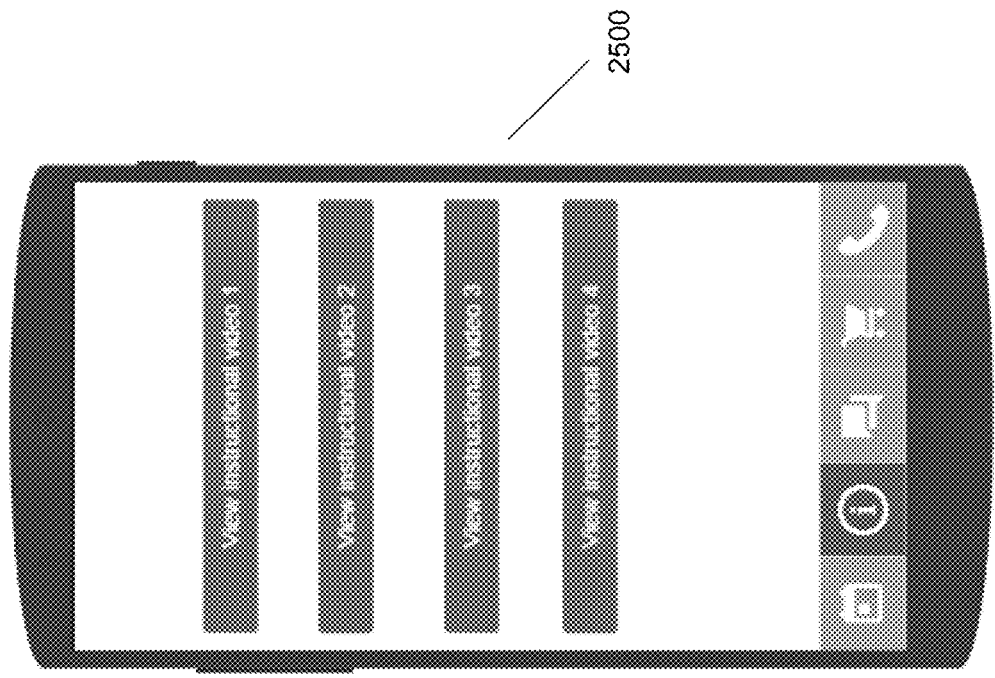
FIG. 25 shows an exemplary instructional video selection page of a patient-side user interface.

Another embodiment of a patient page is described with reference to FIG. 25. FIG. 25 depicts page 2500, which depicts an instructional video selection screen including a plurality of selectable links providing the user access to instructional videos related to using the catheter to drain fluid from the patient. Page 2500 can be reached upon the user selecting the "Watch instructional videos" link of page 2100.

Patient device 201a is further configured to encrypt and store catheter management information in a HIPAA compliant manner, and to transmit catheter management information to server 202 in a HIPAA compliant manner. For example, patient device 201a may be configured to verify that server 202 is located within the same country as the patient device 201a before transmitting catheter management information to the server 202.

One or more patient devices (e.g. patient device 201a), physician devices (e.g. physician device 203), nurse devices (e.g. nurse device 204), and/or servers (e.g. 202) may be configured to receive information from one or more attachments and/or sensors.

The one or more attachments and/or sensors may be of one or more types. For example, one or more of patient device 201a, server 202, physician device 203, and/or nurse device 204 may be further configured to receive information from one or more attachments and/or sensors that include: pH sensors configured to measure the pH level of the drainage fluid, weight sensors configured to measure the weight of the drainage bottle, albumin sensors configured to measure the albumin level of the drainage fluid, intrapleural pressure sensors attached to the catheter, lactate dehydrogenase (LDH) sensors configured to measure LDH level of the drainage fluid, glucose sensors configured to measure glucose level of the drainage fluid, cell count sensors configured to measure cell count level of the drainage fluid, cell differential sensors configured to measure cell differentiation level of the drainage fluid, interleukin (IL) level sensors configured to measure levels of various interleukins of the drainage fluid, vascular endothelial growth factor (VEGF) sensors configured to measure level of VEGF of the drainage fluid, interferon gamma (IFN-gamma) sensors configured to measure level of IFN-gamma of the drainage fluid, and/or other suitable sensors.

In some embodiments, the types of attachments and/or sensors may be different between systems configured to perform and/or monitor different types of drainage. For example, in a system configured to drain fluid and monitor drainage in association with pleural effusion, sensors may include one or more sensors to measure LDH, glucose, pH, cell count, and/or cell differential. In a system configured to drain fluid and monitor drainage in association with ascites, sensors may include one or more sensors to measure cell count, cell differential, IL-6, IL-7, IL-8, IL-9, IL-10, VEGF, IFN-gamma, and/or albumin. These exemplary embodiments are not limiting, and those skilled in the art may recognize other suitable sensor types, and/or combinations of sensor types, with which to configure a patient device, physician device, nurse device, and/or server for communication, and/or to include with a drainage apparatus.

The one or more attachments and/or sensors may be included on or in one or more components of a drainage apparatus such as apparatus 100. One or more sensors may be included on or in a catheter, for example catheter 112. One or more sensors may be included at a distal tip of a catheter, for example catheter 112. One or more sensors may be included in a cap on a catheter valve, for example valve 116. One or more sensors may be included inside drainage tubing, for example proximal tube 110. One or more sensors may be included on or within a drainage container, for example drainage container 114. These exemplary embodiments are not limiting, and those skilled in the art may recognize other suitable sensor locations.

One or more of patient device 201a, server 202, physician device 203, and/or nurse device 204 may be further configured to add data received from these one or more attachments and/or sensors to a patient's historical data log, patient reports, etc., for example in association with a catheter use information entry, and to perform trend analysis on data received from these one or more attachments or sensors.

Referring again to FIGS. 2 and 3, an embodiment of physician device 203 may be implemented using another mobile device 300. In an embodiment of physician device 203 implemented using another mobile device 300, physician device 203 is configured to prompt, using output interface 302, a physician to input catheter use information, and to allow the physician to input catheter use information using input interface 303. In an embodiment of physician device 203 implemented using another mobile device 300, the physician device 203 is further configured to receive the catheter use information that is input by the physician through input interface 303 of user interface 301, and to generate catheter management information based upon the received catheter use information.

In an embodiment of physician device 203 implemented using another mobile device 300, an embodiment of user interface 301 may be a graphical user interface including one or more physician pages configured to be displayed by display 306. Physician device 203 may be configured to generate and/or otherwise provide physician pages for display by display 306. For example, physician device 203 may be configured to render physician pages for display by display 306. Physician pages may each incorporate one or more perceptible output elements 304 and/or one or more interactive input elements 305. As will be described further below, some physician pages may be operatively connected with other physician pages, such that when the physician interacts with an interactive input element 305 on one physician page, another physician page is provided and/or displayed by display 306. Exemplary physician pages with one or more of these features are shown in and described with reference to FIGS. 26-28

Physician device 203 may be further configured to establish a unique physician portal. A unique physician portal may include access to different options, such as different prompts for catheter use information and different catheter management information, than is available in unique patient portals described above and unique nurse portals that are described further below. The unique physician portal may be a secure portal. For example, physician device 203 may be configured such that in order for a physician to view any of the exemplary physician pages of FIGS. 26-28 that display or allow the physician to input catheter use information associated with a physician, the physician must first enter, in a login page similar login page 400, a username associated with the physician along with a password that physician device 203 recognizes as being associated with the physician.

Figure 26:
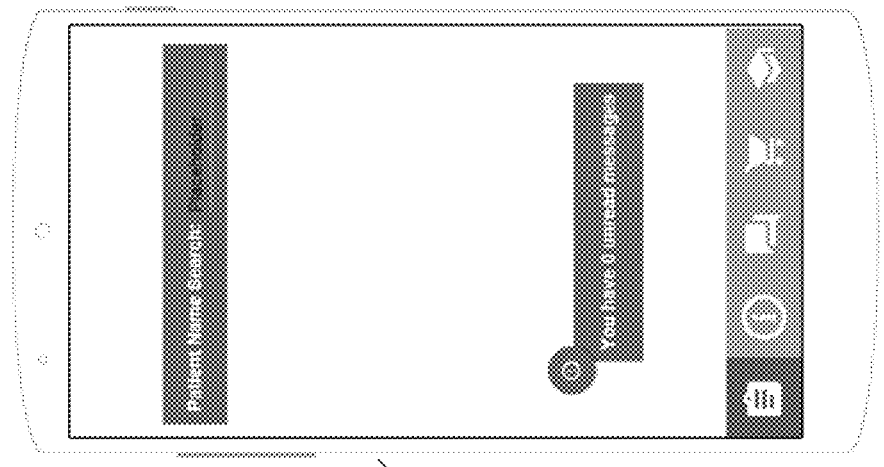
FIG. 26 shows an exemplary physician dashboard page of a physician-side user interface.

An embodiment of a physician page is described with reference to FIG. 26. FIG. 26 depicts page 2600, which is a physician dashboard screen configured to display a plurality of perceptible output elements and a plurality of interactive input elements. Page 2600 is configured to display to the physician an indicator of unread messages associated with the physician, and a fillable text field configured to allow the physician to enter a patient name to search for information related to that patient. Page 2600 is further configured to display to the physician an interactive menu of selectable links to other exemplary physician pages of FIGS. 26-28.

Figure 27:
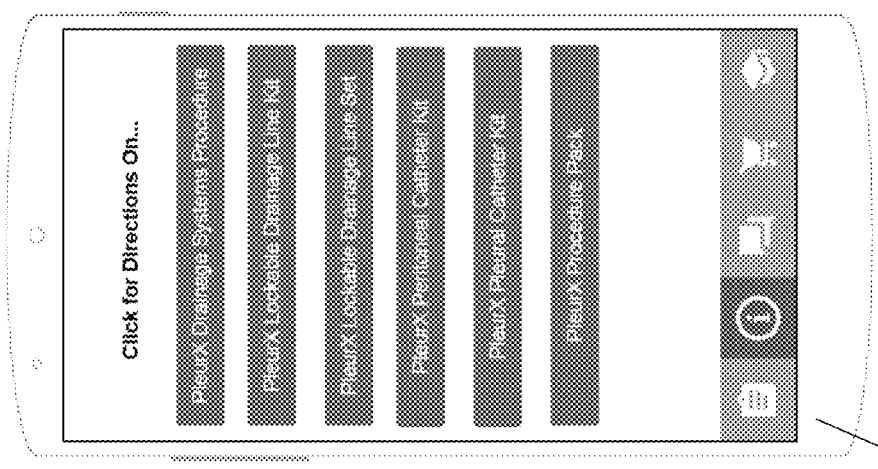
FIG. 27 shows an exemplary directions menu page of a physician-side user interface.

Another embodiment of a physician page 900 is described with reference to FIG. 27. FIG. 27 depicts page 2700, which is a directions menu screen. Page 2700 is configured to allow the physician to request directions regarding a plurality of components related to using a catheter to drain fluid from a patient, by selecting from a plurality of selectable links. Page 2700 can be reached upon a physician selecting the information ("i") selectable link on page 2600.

Figure 28:
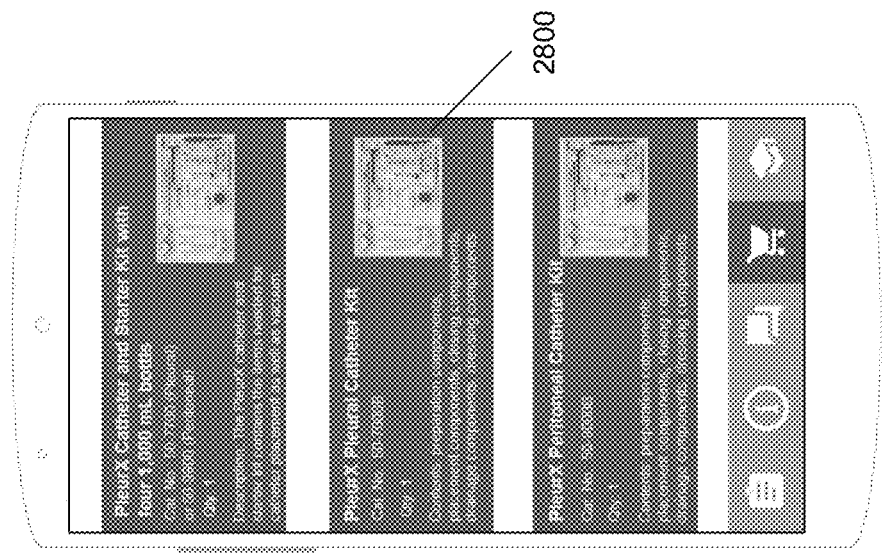
FIG. 28 shows an exemplary shopping menu page of a physician-side user interface.

Another embodiment of a physician page is described with reference to FIG. 28. FIG. 28 depicts page 2800, which is a shopping menu screen. Page 2800 is configured to allow the physician to order components related to using a catheter to drain fluid from a patient, by selecting from a plurality of selectable links. Page 2800 can be reached upon a physician selecting the shopping cart selectable link on page 2600.

Physician device 203 may be further configured to allow the physician to receive, view, and respond to any catheter management information transmitted from patient device 201*a* to physician device 203. Physician device 203 may be configured to allow the physician to view and respond to catheter management information of patient device 203 in real-time. For example, a physician could use physician device 203 to monitor the patient's logged drainage results information, determine that the user is not performing the prescribed drainage procedure, and then use physician device 203 to transmit a message to patient device 201*a* indicating that the prescribed drainage procedure should be adopted immediately to avoid a hospital visit. Physician device 203 may be further configured to transmit a notification to the patient that the patient may need to come in for a follow-up appointment, based upon catheter management information received by the physician device 203.

Referring again to FIGS. 2 and 3, an embodiment of nurse device 204 may be implemented using another mobile device 300. In an embodiment of nurse device 204 implemented using another mobile device 300, nurse device 204 is configured to prompt, using output interface 302, a nurse to input catheter use information, and to allow the nurse to input catheter use information using input interface 303. For example, nurse device 204 may be configured to generate and/or otherwise provide nurse pages for display by display 306. For example, nurse device 204 may be configured to render nurse pages for display by display 306. In an embodiment of nurse device 204 implemented using another mobile device 300, the nurse device 204 is further configured to receive the catheter use information that is input by the nurse through input interface 303 of user interface 301, and to generate catheter management information based upon the received catheter use information.

Nurse device 204 may be further configured to establish a unique nurse portal. A unique nurse portal may include access to different options, such as different prompts for catheter use information and different catheter management information, than is available in unique patient and physician portals that are described above. The unique nurse portal may be a secure portal. For example, nurse device 204 may be configured such that in order for a nurse to view or input catheter use information associated with the nurse, the nurse must first enter, in a login page similar login page 400, a username associated with the nurse along with a password that nurse device 204 recognizes as being associated with the nurse.

In some embodiments of system 200, the same software application could be loaded on or otherwise provided to patient devices 201*a*-201*n*, physician device 203, and nurse device 204, with the software application configured to cause those devices to perform the operations associated herein with those devices. In those embodiments, the software application could be configured such that each device would provide access to the operations respectively associated with that device based upon privileges associated with the username entered in a login page similar to login page 400.

In some embodiments of system 200, two distinct software applications could be provided: a patient software application loaded on or otherwise provided to patient devices 201*a*-201*n*; and a clinician software application loaded on or otherwise provided to physician device 203 and nurse device 204. In those embodiments, the patient software application may be configured to cause patient devices 201*a*-201*n* to perform only the operations associated herein with patient devices 201*a*-201*n*, while the clinician software application may be configured to cause physician device 203 and nurse device 204 to perform the operations respectively associated herein with those devices depending upon privileges associated with the username entered in a login page similar to login page 400. The clinician software application may further be configured to cause both physician device 203 and nurse device 204 to generate a clinician portal that provides access to training opportunities (e.g. webinars), journal articles, discussion boards, videos, tips and tricks, the ICD-10 code list, and/or instructions for how to fill out prescription forms for success with medical supply companies.

Referring again to FIG. 2, server 202 is configured to receive catheter management information transmitted by patient device 201a, physician device 203, and nurse device 204. Server 202 may be a server associated with Amazon Web Services that is configured to host information associated with system 200. Server 202 is configured to encrypt and store received catheter management information in a HIPAA compliant manner. Server 202 is further configured to transmit stored catheter management information in a HIPAA compliant manner to patient device, 201a, physician device 203 and nurse device 204. Server 202 is also configured to transmit catheter management information received from patient device 201a, physician device 203, nurse device 204 to another patient device, another physician device, and/or another nurse device in a HIPAA compliant manner.

In some embodiments, server 202 is further configured to integrate catheter management information received from patient device 201a into electronic health records (EHR) associated with the patient. For example, server 202 may be configured to directly integrate catheter management information into electronic health records associated with the patient, without any intervention by medical personnel. In some embodiments, server 202 is further configured to scrub patient identifying information from catheter management information received from patient device 201a, and to provide the catheter management information, scrubbed of the patient identifying information, to an account associated with a clinical study and/or to an account associated with a manufacturer of the catheter to be used for researching trends in diseases. Scrubbing of patient identifying information may be performed using currently available or later developed algorithms and/or devices recognized as suitable to one skilled in the art. In some embodiments, server 202 is further configured to aggregate catheter management data from a plurality of patient devices 201a-201n for use in clinical studies or for researching trends in diseases.

Figure 29A:
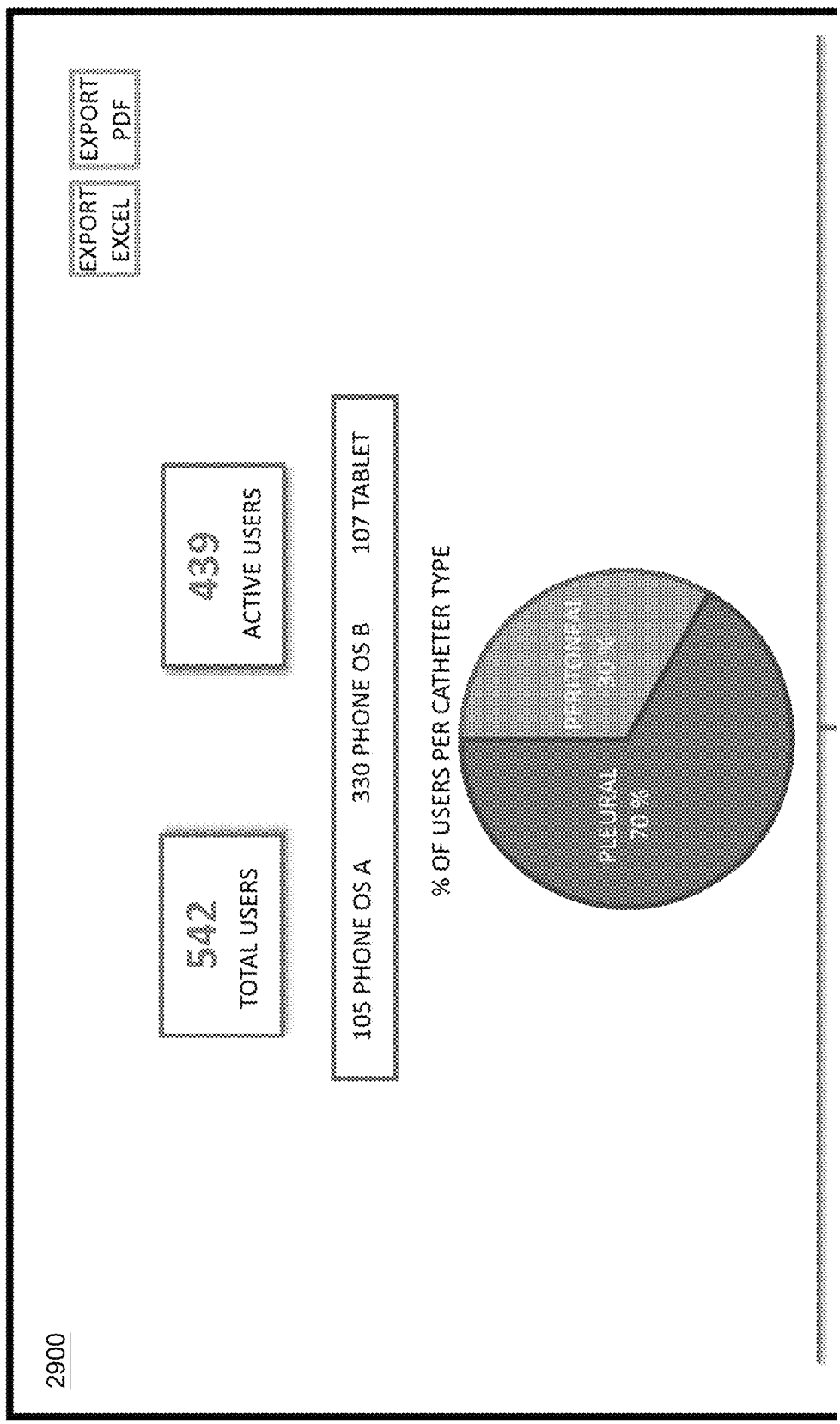
FIGS. 29A and 29B respectively show partial views of a top portion and a bottom portion of an exemplary web portal.
Figure 29B:
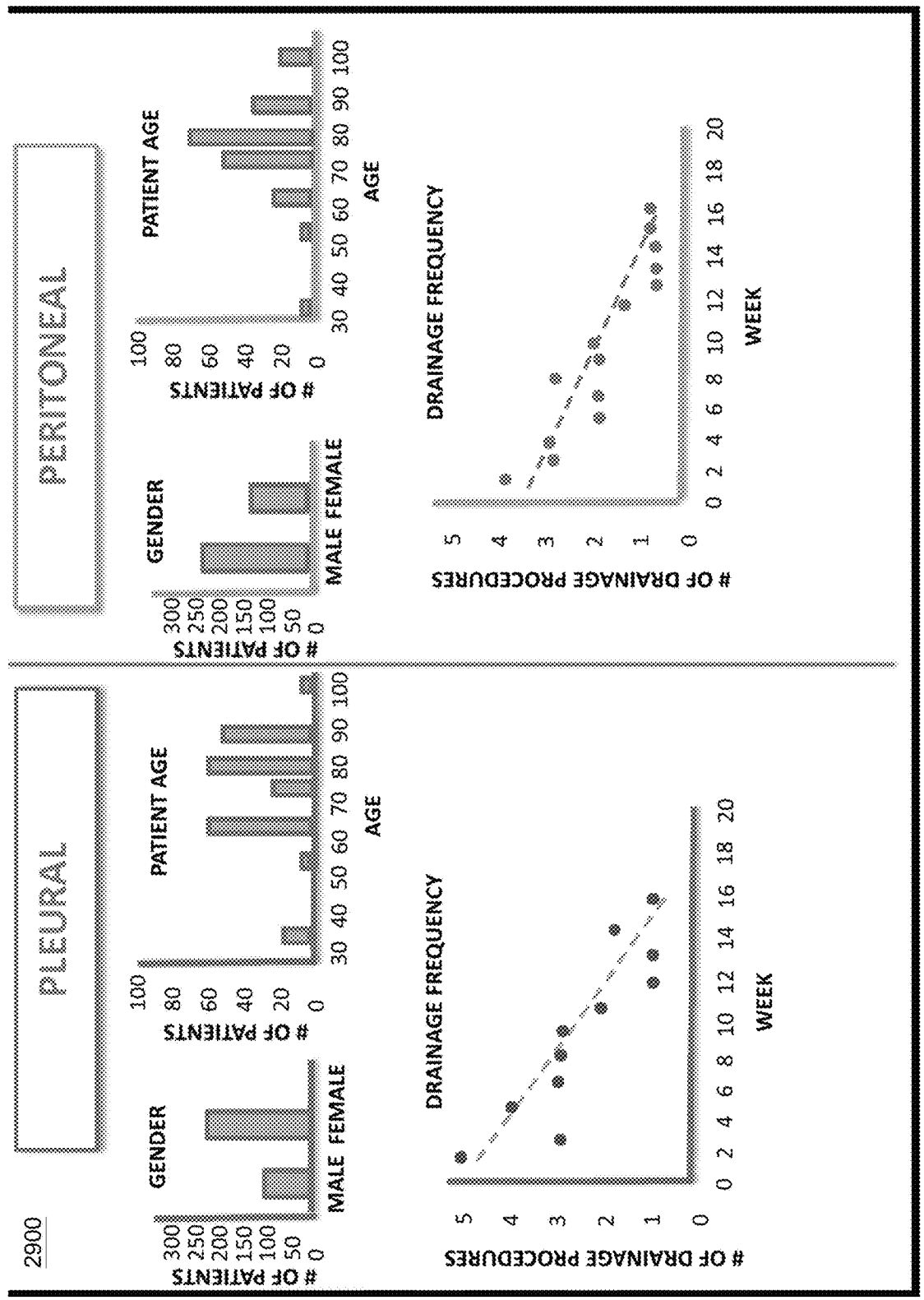

In an exemplary embodiment, server 202 may be configured to analyze aggregated catheter management data from a plurality of patient devices 201a 201n and output population catheter management data to a web portal. An exemplary web portal 2900 output by server 202 is depicted in FIGS. 29A and 29B. Web portal 2900 may be accessible to a manufacturer of the type or brand of catheters that are used by the patients associated with patient devices 201a 201n. As shown in FIGS. 29A and 29B, population catheter management data displayed at web portal 2900 may include: total number of users; number of active users; number of users using a particular type of mobile device; percentage of users using various catheter types (e.g. pleural vs. peritoneal); number of patients of a given gender; number of patients of a given age; and/or average population drainage frequency for a given week of treatment. Population catheter management data displayed at a web portal may also include: average population drainage volume for a given number of drainage procedures; average population pain rating for a given number of drainage procedures; number of patients using a given number of bottles per catheter or performing a given number of drainage entries per catheter; population average amount of time to perform a drainage procedure; population average number of drainage entries per given location; and/or population average number of drainage entries per given performer of drainage. Server 202 may be configured to determine population management data specific to a given type of catheter type (e.g. pleural vs. peritoneal).

Figure 30:
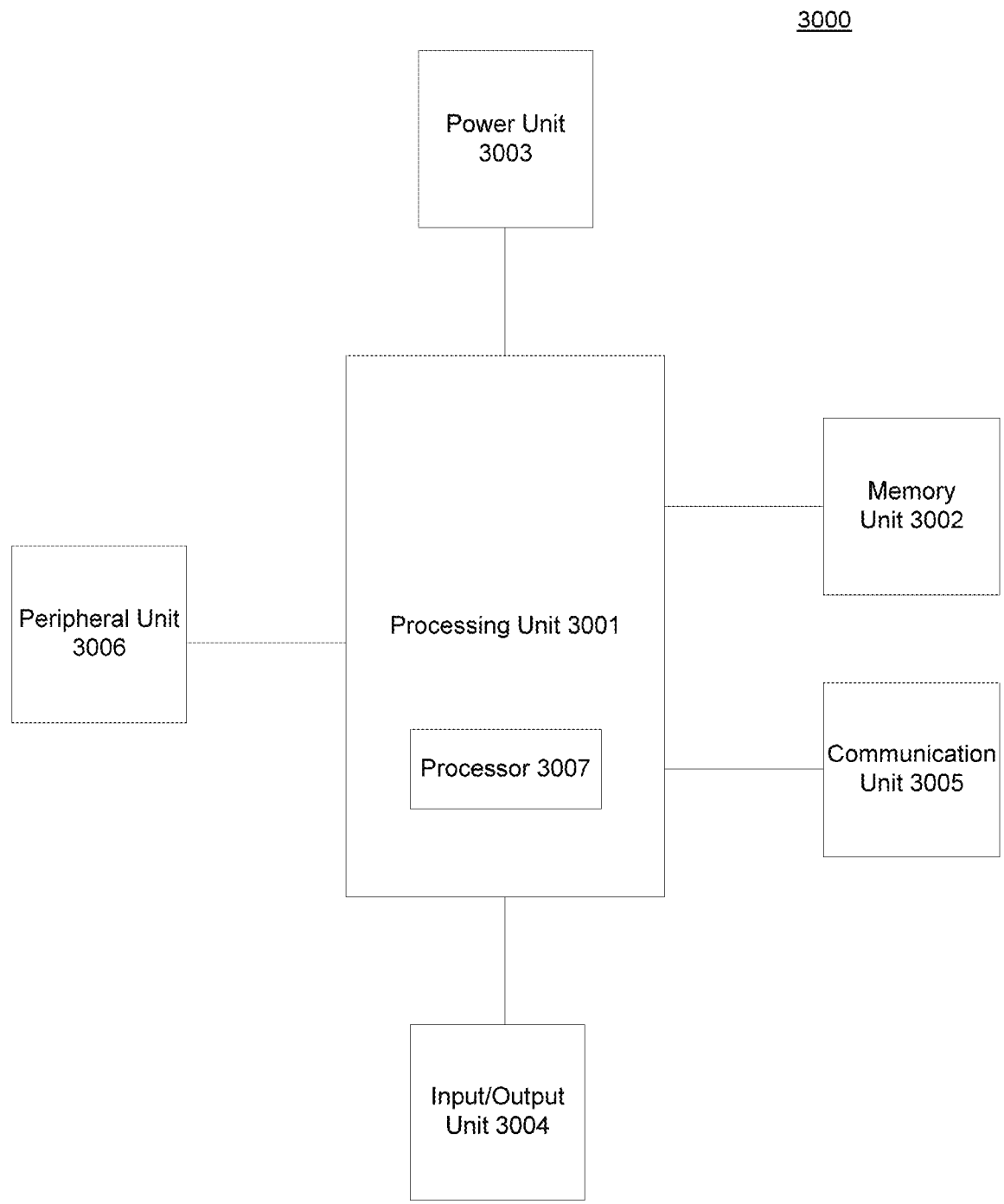
FIG. 30 shows an exemplary electronic device.

One embodiment of an electronic device having elements suitable for implementing patient device 201a, server 202, physician device 203, nurse device 204, and/or mobile device 300 is described with reference to FIG. 30, which depicts electronic device 3000. Electronic device 3000 may be a mobile phone, smart phone, tablet computer, desktop computer, laptop computer, personal digital assistant (PDA), medical device, dedicated server, or the like, as appropriate given the context. Electronic device 3000 includes a processing unit 3001 operably connected with a memory unit 3002, a power unit 3003, an input/output unit 3004, a communication unit 3005, and a peripheral unit 3006.

Processing unit 3001 includes one or more of processor 3007. Processor 3007 is configured to receive, process, and output data. Processor 3007 may be or include one or more of a microprocessor, central processing unit (CPU), application specific integrated circuit (ASIC), digital signal processor (DSP), network processor, graphics processing unit, floating-point unit, image processor, coprocessor, or the like.

Memory unit 3002 is generally configured to store data in a manner accessible to one or more of the other units of electronic device 3000. Memory 3002 may include a non-transitory computer-readable medium. Memory unit 3002 may include one or more of non-volatile memory, including flash memory, read-only memory (ROM), programmable ROM (PROM), erasable PROM (EPROM), and, electrically erasable PROM (EEPROM), or volatile memory, including dynamic random-access memory (DRAM), fast CPU cache memory, static random-access memory (SRAM), or the like. Memory unit 3002 may be configured to receive, organize, and store data received from one or more of the other units of electronic device 3000, and allow one or more of the other units of electronic device 3000 to access the data stored by the memory unit 3002 as appropriate in context.

Memory unit 3002 may store software or firmware in the form of a set of executable instructions configured to be executed by processing unit 3001. The set of executable instructions stored by memory unit 3002 may be configured to, when executed by processing unit 3001, cause processing unit 3001 to perform, or as appropriate according to context, control the performance of, any of the operations associated in this disclosure with system 200, patient device 201a, server 202, physician device 203, nurse device 204, or mobile device 300.

Power unit 3003 generally provides power to one or more of the other units of electronic device 3000 to allow those units to function. Power unit 3003 may include an AC or DC power supply, switches, a current regulator, and a voltage regulator. Power unit 3003 may include a battery or other source of electrical energy.

Input/output unit 3004 is configured to provide for transfer of information between processing unit 3001 and one or more of memory unit 3002, communication unit 3005, or peripheral unit 3006. Input/output unit 3004 may be implemented as hardware, software, or a combination of hardware and software.

Communication unit 3005 is configured to receive data for and transmit data from electronic device 3000. Communication unit 3005 may facilitate wired or wireless communication with other devices. Communication unit 3005 may include a wireless antenna and/or transceiver. Communication unit 3005 may be configured to establish a data transfer connection with a computer network such as the internet, or with individual devices. Communication unit 3005 may be configured to communicate according to any communication protocol recognized as suitable in the art.

Peripheral unit 3006 is configured to accept input from a user or output information to a user. Peripheral unit 3006 may include input peripherals such as a keyboard, computer mouse, touchscreen, microphone, digital camera, image capture sensor, video sensor, or the like. Peripheral unit 3006 may further include output peripherals, such as a computer display, speaker, or the like. Peripheral unit 3006 may further be configured to accept input from one or more attachments and/or sensors configured to provide information about the catheter use, including pH sensors, weight sensors, albumin level sensors, intrapleural pressure sensors, LDH level sensors, glucose level sensors, cell count sensors, cell differential level sensors, IL level sensors, VEGF level sensors, IFN-gamma level sensors, and/or other suitable sensors.

Aspects of this disclosure provide a variety of benefits over the conventional paper log technology discussed above. Devices for and methods of mobile monitoring of a drainage catheter disclosed herein may: allow users to more conveniently log information related to the drainage catheter and share the information with parties involved in the treatment; provide for automatic notification of relevant conditions to parties involved in the treatment; allow for parties involved in the treatment to access unique portals and dashboards targeted to the respective parties' roles in the treatment; allow the patient to more efficiently obtain necessary drainage supplies and communicate with other patients using the same type of catheter; and/or increase patient compliance with prescribed drainage procedures and thereby improve patient outcomes.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A non-transitory computer-readable medium storing instructions configured to be executed by a processor, wherein the instructions are configured to, when executed by the processor, cause the processor to perform operations of:
rendering a user interface configured to:
provide an output interface configured to prompt a user to input catheter use information, catheter use information being information related to using the catheter to drain fluid from a patient; and
provide an input interface for the user to input catheter use information; receiving catheter use information input by the user through the user interface; and
generating catheter management information based upon the received catheter use information;
wherein the output interface is configured to prompt the user to input, as catheter use information, an image of a drainage bottle used in association with the catheter to drain fluid from the patient; and
wherein the instructions are configured to cause the processor to generate the catheter management information by performing image analysis of the image of the drainage bottle.

2. The non-transitory computer-readable medium of claim 1, wherein the instructions are configured to cause the processor to generate the catheter management information by:
determining whether medical personnel should be contacted regarding the patient; and
providing, in accordance with a result of the determining, an indication of whether medical personnel should be contacted regarding the patient.

3. The non-transitory computer-readable medium of claim 2, wherein the instructions are configured to cause the processor to perform the determining of whether medical personnel should be contacted regarding the patient by determining whether the catheter use information indicates that the patient is exhibiting a predetermined condition.

4. The non-transitory computer-readable medium of claim 3, wherein the instructions are configured to cause the processor to, when the patient is determined to be exhibiting the predetermined condition, automatically contact a medical professional regarding the patient.

5. The non-transitory computer-readable medium of claim 1, wherein the instructions are configured to cause the processor to generate the catheter management information by providing, based upon the received catheter use information, a recommendation of a step to be taken by the user to use the catheter to drain fluid from the patient.

6. The non-transitory computer-readable medium of claim 5, wherein the recommendation of the step to be taken by the user to use the catheter to drain fluid from the patient comprises at least one of:
a page configured to request a new prescription for a component of using the catheter to drain fluid from the patient;
a page configured to order a component of using the catheter to drain fluid from the patient;
instructions for how to use the catheter to drain fluid from the patient;
instructions for when to next use the catheter to drain fluid from the patient; or
a page configured to access a video file related to using the catheter to drain fluid from the patient.

7. The non-transitory computer-readable medium of claim 1, wherein the instructions are further configured to cause the processor to encrypt the catheter management information and to provide the encrypted catheter management information to a server, the server being accessible to medical personnel through a secure portal associated with the medical personnel.

8. The non-transitory computer-readable medium of claim 1, wherein the output interface is configured to prompt the user to input catheter use information comprising at least one of: drainage volume from the patient; drainage frequency of the patient; catheter exit site infections of the patient; ambulatory ability of the patient; a date of a drainage of the patient; a time of a drainage of the patient; a discomfort level of the patient; a portion of body of the patient from which a drainage is obtained; or an image of a drainage bottle used in association with the catheter to drain fluid from the patient.

9. The non-transitory computer-readable medium of claim 1, wherein the instructions are further configured to cause the processor to perform operations of:
   displaying a secure portal that is associated with the patient, the secure portal requiring that the user enter credentials associated with the patient to access the secure portal; and
   in response to the user accessing the secure portal:
      allowing the output interface to prompt the user to input catheter use information; and
      allowing the user to input catheter use information with the input interface.

10. A method for mobile monitoring of a catheter to drain fluid from a patient, comprising:
   rendering, by a processor, a user interface configured to:
      provide an output interface configured to prompt a user to input catheter use information, catheter use information being information related to using the catheter to drain fluid from the patient; and
      provide an input interface for the user to input catheter use information;
   receiving, by a processor, catheter use information input by the user through the user interface; and
   generating, by a processor, catheter management information based upon the received catheter use information;
   wherein the output interface is configured to prompt the user to input, as catheter use information, an image of the drainage bottle used in association with the catheter to drain fluid from the patient, and
   further comprising generating, by a processor, the catheter management information by performing image analysis of the image of the drainage bottle.

11. The method of claim 10, wherein generating the catheter management information comprises: determining, by a processor, whether medical personnel should be contacted regarding the patient; and
   providing, by a processor, in accordance with a result of the determining, an indication of whether medical personnel should be contacted regarding the patient.

12. The method of claim 11, wherein the determining of whether medical personnel should be contacted regarding the patient comprises determining, by a processor, whether the catheter use information indicates that the patient is exhibiting a predetermined condition.

13. The method of claim 12, further comprising, when the patient is determined to be exhibiting the predetermined condition, automatically contacting, by a processor, a medical professional regarding the patient.

14. The method of claim 10, wherein generating the catheter management information comprises providing, by a processor, based upon the received catheter use information, a recommendation of a step to be taken by the user to use the catheter to drain fluid from the patient.

15. The method of claim 14, wherein the recommendation of the step to be taken by the user to use the catheter to drain fluid from the patient comprises at least one of:
   a page configured to request a new prescription for a component of using the catheter to drain fluid from the patient;
   a page configured to order a component of using the catheter to drain fluid from the patient;
   instructions for how to use the catheter to drain fluid from the patient;
   instructions for when to next use the catheter to drain fluid from the patient; or
   a page configured to access a video file related to using the catheter to drain fluid from the patient.

16. The method of claim 10, further comprising encrypting, by a processor, the catheter management information and providing, by a processor, the encrypted catheter management information to a server, the server being accessible to medical personnel through a secure portal associated with the medical personnel.

17. The method of claim 10, wherein the output interface is configured to prompt the user to input catheter use information comprising at least one of: drainage volume from the patient; drainage frequency of the patient; catheter exit site infections of the patient; ambulatory ability of the patient; a date of a drainage of the patient; a time of a drainage of the patient; a discomfort level of the patient; a portion of body of the patient from which a drainage is obtained; or an image of a drainage bottle used in association with the catheter to drain fluid from the patient.

18. The method of claim 10, further comprising:
   generating, by a processor, a secure portal that is associated with the patient, the secure portal requiring that the user enter credentials associated with the patient to access the secure portal; and in response to the user accessing the secure portal:
   allowing, by the processor, the output interface to prompt the user to input catheter use information; and
   allowing, by the processor, the user to input catheter use information with the input interface.

* * * * *